US007192412B1

(12) United States Patent
Zhou et al.

(10) Patent No.: US 7,192,412 B1
(45) Date of Patent: Mar. 20, 2007

(54) TARGETED STENT PLACEMENT AND MULTI-STENT THERAPY

(75) Inventors: Jianbo Zhou, Rancho Santa Margarita, CA (US); Gregory Smedley, Aliso Viejo, CA (US)

(73) Assignee: Glaukos Corporation, Laguna Hills, CA (US)

( * ) Notice: Subject to any disclaimer, the term of this patent is extended or adjusted under 35 U.S.C. 154(b) by 372 days.

(21) Appl. No.: 10/662,696

(22) Filed: Sep. 15, 2003

Related U.S. Application Data

(60) Provisional application No. 60/410,646, filed on Sep. 14, 2002, provisional application No. 60/432,861, filed on Dec. 12, 2002, provisional application No. 60/438,372, filed on Jan. 7, 2003.

(51) Int. Cl.
*A61M 5/00* (2006.01)
(52) U.S. Cl. .......................................................... 604/8
(58) Field of Classification Search .............. 600/398, 600/399; 604/8–10, 521; 623/4.1, 905; 606/108
See application file for complete search history.

(56) References Cited

U.S. PATENT DOCUMENTS

| | | | |
|---|---|---|---|
| 4,521,210 A | | 6/1985 | Wong |
| 4,936,825 A | | 6/1990 | Ungerleider |
| 5,178,604 A | | 1/1993 | Baerveldt et al. |
| 5,807,302 A | * | 9/1998 | Wandel .......................... 604/8 |
| 6,464,724 B1 | * | 10/2002 | Lynch et al. .................. 623/4.1 |
| 6,494,857 B1 | * | 12/2002 | Neuhann ........................ 604/8 |
| 6,533,768 B1 | * | 3/2003 | Hill ............................. 604/521 |
| 6,638,239 B1 | * | 10/2003 | Bergheim et al. ............. 604/27 |
| 2002/0013572 A1 | * | 1/2002 | Berlin ............................ 606/4 |
| 2002/0188308 A1 | * | 12/2002 | Tu et al. ...................... 606/167 |

OTHER PUBLICATIONS

Robert A. Moses, M.D.; Circumferential Flow in Schlemm's Canal; *American Journal of Ophthalmology*; Sep. 1979; vol. 88, No. 3, Part II, :pp. 585-591.
Barbara A. Smit, M.D., Ph.D. & Murray A. Johnstone, M.D.; Effects of Viscoelastic Injection into Schlemm's Canal in Primate and Human Eyes; *American Academy of Ophthalmology*; Apr. 2002; vol. 109, No. 4; pp. 786-792.
Robert A. Moses, Walter J. Grodzki, Jr., Ellen L. Etheridge, and Carolyn D. Wilson; Schlemm's Canal: The Effect of Intraocular Pressure; *Investigative Ophthalmology & Visual Science*; Jan. 1981; vol. 20, No. 1; pp. 61-68.
M.C. Johnson and R. D. Kamm; The Role of Schlemm's Canal in Aqueous Outflow from the Human Eye; *Investigative Ophthalmology*; Mar. 1983; vol. 24, pp. 321-325.
Detlev Spiegel, Marion Schefthaler, & Karin Kobuch; Outflow Facilities Through Decsement's Membrane in Rabbits; *Graefe's Arch Clin Exp. Ophthalmolgy*; Jan. 2002, No. 240, pp. 111-113.
Douglas H. Joohnson, M.D. and Mark Johnson, Ph.D.; Basic Sciences in Clinical Glaucoma: How Does Nonpenetrating Glaucoma Surgery Work? Aqueous Outflow Resistance and Glaucoma Surgery; *Journal of Glaucoma*; 2001, vol. 10, No. 1, pp. 55-67.

* cited by examiner

*Primary Examiner*—Max F. Hindenburg
*Assistant Examiner*—Michael Apanius
(74) *Attorney, Agent, or Firm*—Knobbe, Martens, Olson & Bear LLP

(57) ABSTRACT

A trabecular flow model for producing treatment recommendations for patients with elevated intraocular pressure is disclosed. One method includes providing intraocular pressure measurements for a patient; providing aqueous cavity information, such as collector channel resistance and Schlemm's canal resistance, and determining a treatment recommendation for the patient based on the aforementioned parameters.

10 Claims, 19 Drawing Sheets

Note: SC: Schlemm's canal, C: Collector channel,
A: Artery, N: Nasal, T: Temporal

| | |
|---|---|
| IOP (mmHg) | 15 |
| Episcleral Venous Pressure (mmHg) | 9 |
| Conventional Outflow (µl/min) | 2.4 |
| Trabecular Meshwork Resistance (mmHg/(µl/min)) | 1.25 |
| Collector Channel Resistance (mmHg/(µl/min)) | 1.25 |
| Schlemm's Canal Resistance (mmHg/(µl/min)/mm) | 1 |
| Facility of Outflow (µl/min/mmHg) | 0.4 |
| Length of Schlemm's Canal (mm) | 36 |
| Viscosity of Aqueous Humor (cP) | 0.7193 |
| Height of Schlemm's Canal (µm) | 20 |
| Width of Schlemm's Canal (µm) | 230 |

FIG. 6. Average parameters for a normal eye with healthy trabecular meshwork

TARGETED STENT PLACEMENT AND MULTI-STENT THERAPY

CROSS REFERENCE TO RELATED APPLICATIONS

This application claims the priority benefits of U.S. Provisional Application No. 60/410,646, filed Sep. 14, 2002; U.S. Provisional Application No. 60/432,861, filed Dec. 12, 2002; and U.S. Provisional Application No. 60/438,372, filed Jan. 7, 2003. The entireties of all of these documents are hereby incorporated by reference.

FIELD OF THE INVENTION

The invention generally relates to medical devices and methods for the reduction of elevated pressure in an eye of a patient. More particularly, the invention relates to the treatment of glaucoma by means of targeted stent placement and multi-stent therapy in an ab externo and/or ab interno procedures for bypassing diseased trabecular meshwork.

BACKGROUND OF THE INVENTION

About two percent of people in the United States have glaucoma. Glaucoma is a group of eye diseases that causes pathological changes in the optic disk and corresponding visual field loss resulting in blindness if untreated. Intraocular pressure elevation is the major etiologic factor in all glaucomas.

In glaucomas associated with an elevation in eye pressure the source of resistance to outflow is in the trabecular meshwork. The tissue of the trabecular meshwork allows the "aqueous" to enter Schlemm's canal, which then empties, into aqueous collector channels in the posterior wall of Schlemm's canal and then into aqueous veins. The aqueous or aqueous humor is a transparent liquid that fills the region between the cornea at the front of the eye and the lens. The aqueous humor is constantly secreted by the ciliary body around the lens, so there is a continuous flow of the aqueous humor from the ciliary body to the eye's front chamber. The eye's pressure is determined by a balance between the production of aqueous and its exit through trabecular meshwork (major route) or uveal scleral outflow (minor route). The trabecular meshwork is located between the outer rim of the iris and the back of the cornea. The portion of the trabecular meshwork adjacent to Schlemm's canal causes most of the resistance to aqueous outflow (juxtacanilicular meshwork).

Glaucoma is grossly classified into two categories: closed-angle glaucoma and open-angle glaucoma. The closed-angle glaucoma is caused by closure of the anterior angle by contact between the iris and the inner surface of the trabecular meshwork. Closure of this anatomical angle prevents normal drainage of aqueous humor from the anterior chamber of the eye. Open-angle glaucoma is any glaucoma in which the angle of the anterior chamber remains open, but the exit of aqueous through the trabecular meshwork is diminished. The exact cause for diminished filtration is unknown for most cases of open-angle glaucoma. However, there are secondary open-angle glaucomas that may include edema or swelling of the trabecular spaces (from steroid use), abnormal pigment dispersion, or diseases such as hyperthyroidism that produce vascular congestion.

All current therapies for glaucoma are directed at decreasing intraocular pressure. This is initially by medical therapy with drops or pills that reduce the production of aqueous humor or increase the outflow of aqueous. However, these various drug therapies for glaucoma are sometimes associated with significant side effects, such as headache, blurred vision, allergic reactions, death from cardiopulmonary complications and potential interactions with other drugs. When the drug therapy fails, surgical therapy is used. Surgical therapy for open-angle glaucoma consists of laser (trabeculoplasty), trabeculectomy and aqueous shunting implants after failure of trabeculectomy or if trabeculectomy is unlikely to succeed. Trabeculectomy is a major surgery that is most widely used and is augmented with topically applied anticancer drugs such as 5-flurouracil or mitomycin-c to decrease scarring and increase surgical success.

Approximately 100,000 trabeculectomies are performed on Medicare age patients per year in the United States. This number would increase if the morbidity associated with trabeculectomy could be decreased. The current morbidity associated with trabeculectomy consists of failure (10–15%), infection (a life long risk about 2–5%), choroidal hemorrhage (1%, a severe internal hemorrhage from pressure too low resulting in visual loss), cataract formation, and hypotony maculopathy (potentially reversible visual loss from pressure too low).

If it were possible to bypass the focal resistance to outflow of aqueous at the point of the resistance and use existing outflow mechanisms, surgical morbidity would greatly decrease. The reason for this is that the episcleral aqueous has a backpressure that would prevent the eye pressure from going too low. This would virtually eliminate the risk of hypotony maculopathy and choroidal hemorrhage. Furthermore, visual recovery would be very rapid and risk of infection would be very small (a reduction from 2–5% to about 0.05%). Because of these reasons surgeons have tried for decades to develop a workable surgery for the trabecular meshwork.

The previous techniques, which have been tried, are goniotomy/trabeculotomy, and other mechanical disruption of the trabecular meshwork, such as trabeculopuncture, goniophotoablation, laser trabecular ablation and goniocurretage. They are briefly described below.

Goniotomy/Trabeculotomy: Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed secondary to repair mechanisms and a process of "filling in". The filling in is a detrimental effect of collapsing and closing in of the created opening throughput trabecular meshwork. Once the created openings close, the pressure builds back up and the surgery fails.

Trabeculopuncture: Q-switched Neodymium (Nd):YAG lasers also have been investigated as an optically invasive technique for creating full-thickness holes in trabecular meshwork. However, the relatively small hole created by this trabeculopuncture technique exhibits a filling in effect and fails.

Goniophotoablation/Laser Trabecular Ablation: Goniophotoablation is disclosed by Berlin in U.S. Pat. No. 4,846,172 and in U.S. patent application Ser. No. 2002/13572 published Jan. 31, 2002, and describes the use of an excimer laser to treat glaucoma by ablating the trabecular meshwork. This was not demonstrated by clinical trail to succeed. Hill et al. used an Erbium:YAG laser to create full thickness holes through trabecular meshwork (Hill et al., Lasers in Surgery and Medicine 11:341–346, 1991). This technique was investigated in a primate model and a limited human clinical trial at the University of California, Irvine. Although morbidity was zero in both trials, success rates did not warrant further human trials. Failure again was from filling in of created defects in trabecular meshwork by repair mechanisms. Neither of these is a valid surgical technique for the treatment of glaucoma.

Goniocurretage: This is a mechanical disruptive technique. This uses an instrument similar to a cyclodialysis spatula with a microcurrette at the tip. Initial results are similar to trabeculotomy that fails secondary to repair mechanisms and a process of filling in.

Although trabeculectomy is the most commonly performed filtering surgery, Viscocanulostomy (VC) and non-penetrating trabeculectomy (NPT) are two new variations of filtering surgery. These are ab-externo (from the outside), major ocular procedures in which Schlemm's canal is surgically exposed by making a large and very deep scleral flap. In the VC procedure, Schlemm's canal is cannulated and viscoelastic substance injected (which dilates Schlemm's canal). In the NPT procedure, the inner wall of Schlemm's canal is stripped off after surgically exposing the canal.

Trabeculectomy, VC, and NPT involve the formation of an opening or hole into the anterior chamber, under the conjunctiva and scleral flap such that the aqueous humor is drained onto the surface of the eye or into the tissues located within the lateral wall of the eye. These surgical operations are major procedures with significant ocular morbidity. When Trabeculectomy, VC, and NPT are thought to have a low chance for success, a number of implantable drainage devices have been used to ensure that the desired filtration and outflow of aqueous humor through the surgical opening will continue. The risk of placing a glaucoma drainage implant also includes hemorrhage, infection and postoperative double vision that is a complication unique to drainage implants.

The above embodiments and variations thereof have numerous disadvantages and moderate success rates. They involve substantial trauma to the eye and require great surgical skill by creating a hole over the full thickness of the sclera/cornea into the subconjunctival space. The procedures are mostly performed in an operating room generating a facility fee, anesthesiologist's professional fee and have a prolonged recovery time for vision. The complications of filtration surgery have inspired ophthalmic surgeons to look at other approaches to lowering intraocular pressure.

The trabecular meshwork and juxtacanilicular tissue together provide the majority of resistance to the outflow of aqueous and, as such, are logical targets for surgical removal in the treatment of open-angle glaucoma. In addition, minimal amounts of tissue are altered and existing physiologic outflow pathways are utilized. Trabecular surgery has the advantage of much lower risks of choroidal hemorrhage, infection and uses existing physiologic outflow mechanisms. This surgery could be performed under topical anesthesia in a physician's office with rapid visual recovery.

SUMMARY OF THE INVENTION

Therefore, there is a clinical need for the treatment of glaucoma by an ab interno Trabecular Bypass Microsurgery method that would be faster, safer and less expensive than currently available modalities.

Trabecular bypass microsurgery creates an opening or a hole through diseased trabecular meshwork from Schlemm's canal in an ab externo procedure or from the anterior chamber in an ab interno procedure. It is one object of the present invention to provide a method for facilitating this "trabecular microsurgery" and subsequently implanting the trabecular stent in a single operation by leaving the outlet end of the stent within Schlemm's canal and the inlet end of the stent within an anterior chamber.

The "ab externo" procedure in this invention is intended to mean implanting a trabecular stent from Schlemm's canal through trabecular meshwork into an anterior chamber. The "ab interno" procedure in this invention is intended to mean implanting a trabecular stent from an anterior chamber through trabecular meshwork into Schlemm's canal.

The stent, or implant, may be made of biocompatible material, which is typically hollow to allow the flow of aqueous humor. The material for the stent may be selected from the group consisting of porous material, semi-rigid material, soft material, hydrophilic material, hydrophobic material, hydrogel, elastic material, meshed material, or expandable/retractable material, and the like. The stent may be loaded with drug for therapeutic effects. In a further embodiment, the drug is slowly released into Schlemm's canal and further into the venous collecting channels.

From trabecular flow modeling, it is calculated that intraocular pressure (IOP) is reduced substantially as the normal canal height (20 µm) increases to a moderately expanded canal height (40~50 µm) at the bypass; the reduction effec tis diminished with further dilation. The Schlemm's canal (SC) dilation is more effective for eyes with smaller SC. The dilation of collector channels (CC) can also significantly lower the IOP. With the trabecular bypass alone, the elevated IOP in a glaucomatous eye is expected to drop to mid-to-high teens on average. The IOP can be further reduced by 3 to 6 mmHg with moderate SC and CC dilation. The dilated SC circumferential length affects the efficacy of IOP reduction. The dilation of SC in conjunction with a trabecular bypass is analogous to a partial trabeculotomy.

Some aspects of the invention include a method of creating a treatment recommendation for a patient with elevated intraocular pressure, the method comprising: providing a baseline intraocular pressure of the patient; providing at least one of a target intraocular pressure and a target reduction in intraocular pressure for the patient; providing at least one aqueous cavity datum, the aqueous cavity datum selected from the group consisting of a collector channel resistance, a Schlemm's canal resistance, a length of a segment Schlemm's canal, a height of Schlemm's canal, and a width of Schlemm's canal; and determining a treatment recommendation for the patient, based on the baseline intraocular pressure of the patient, the at least one of a target intraocular pressure or a target reduction in intraocular pressure for the patient, and the at least one aqueous cavity datum; wherein the treatment recommendation comprises at least one of a recommended location of a stent implantation and a recommended number of stents to be implanted.

In some embodiments, the recommended location of a stent implantation comprises a distance from a collector channel. In some embodiments, this distance is measured along Schlemm's canal.

In some aspects of the invention, the method further comprises providing at least one additional ocular datum, the at least one additional ocular datum selected from the group consisting of an episcleral venous pressure, a trabecular meshwork resistance, a facility of outflow, and a viscosity of aqueous humor; wherein the treatment recommendation is also based on the at least one additional ocular datum.

Some aspects of the invention include a method of creating a treatment recommendation for a patient with elevated intraocular pressure, the method comprising: providing a baseline intraocular pressure of the patient; providing at least one of a target intraocular pressure and a target reduction in intraocular pressure for the patient; providing at least one of a location of at least one collector channel and a distribution of a plurality of collector channels; and determining a treatment recommendation for the patient, based on the baseline intraocular pressure of the patient, the at least one of a target intraocular pressure or a target reduction in intraocular pressure for the patient, and the at least one of a location of at least one collector channel and a distribution of a plurality of collector channels; wherein the treatment recommendation comprises at least one of a recommended location of a stent implantation and a recommended number of stents to be implanted.

In some embodiments, the recommended location of a stent implantation is selected from the group consisting of nasal, temporal, a quadrantic position, and a clock-hour position.

In some embodiments, the distribution of a plurality of collector channels is determined by imaging the patient. In some embodiments, the distribution of a plurality of collector channels is determined at least in part from statistical data from eyes other than the patient's eyes.

Some aspects of the invention relate to a method for implanting a trabecular stent to lower intraocular pressure of an eye comprising: providing the trabecular stent, wherein the stent comprises an inlet terminal and an outlet terminal, means for identifying a target collector channel region that connects to peripheral of Schlemm's canal, and placing the trabecular stent through trabecular meshwork, wherein the inlet terminal is exposed to an anterior chamber and the outlet terminal is exposed to about the target collector channel region. In one embodiment, the means for identifying the target collector channel region is by observing the reflux of blood toward Schlemm's canal or by applying trabecular flow modeling.

Some aspects of the invention relate to a method for achieving a target intraocular pressure of an eye, comprising: providing a bypass flow model, wherein the model simulates hydrodynamic aqueous flow from an anterior chamber to aqueous cavity, and wherein the model comprises a data input requirement and a data output statement, identifying aqueous cavity parameters, selecting a trabecular stent, wherein the stent comprises an inlet terminal and at least one outlet terminal, performing the bypass flow model by keying in the data input requirement, including at least one parameter selected from the aqueous cavity parameters, and obtaining the data output statement through the model, wherein the statement includes a decision selected from a group consisting of a number of trabecular stents needed, a location of the trabecular stent implanted, and type of the trabecular stent. In one embodiment, the method comprises a step of implanting a second and/or third trabecular stent at a later time.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

FIG. 6 shows average parameters for a normal eye with healthy trabecular meshwork.

DETAILED DESCRIPTION OF THE PREFERRED EMBODIMENT

Referring to FIGS. 1 to 19, a method for the treatment of glaucoma by implanting at least one stent implant targeted at or near to the collector channels is shown. In particular, a trabecular bypass flow model is developed and applied to exploit the effect of Schlemm's canal (SC) and collector channel (CC) dilation on intraocular pressure (IOP), enabling targeting optimal site or regions for stent placement.

In the trabecular bypass flow model, the elliptic shaped SC is dilated in conjunction with a trabecular bypass and its expanded height is largest at the bypass and linearly decreases to the non-diluted height over the diluted circumferential length. The dilation of CC is modeled with a reduced outflow resistance of second order polynomial over the same dilated length. Equations governing the pressure and circumferential flow is SC are solved numerically for both the unidirectional and bidirectional bypasses. The reduced IOP is deduced from the solution.

Figure 1:
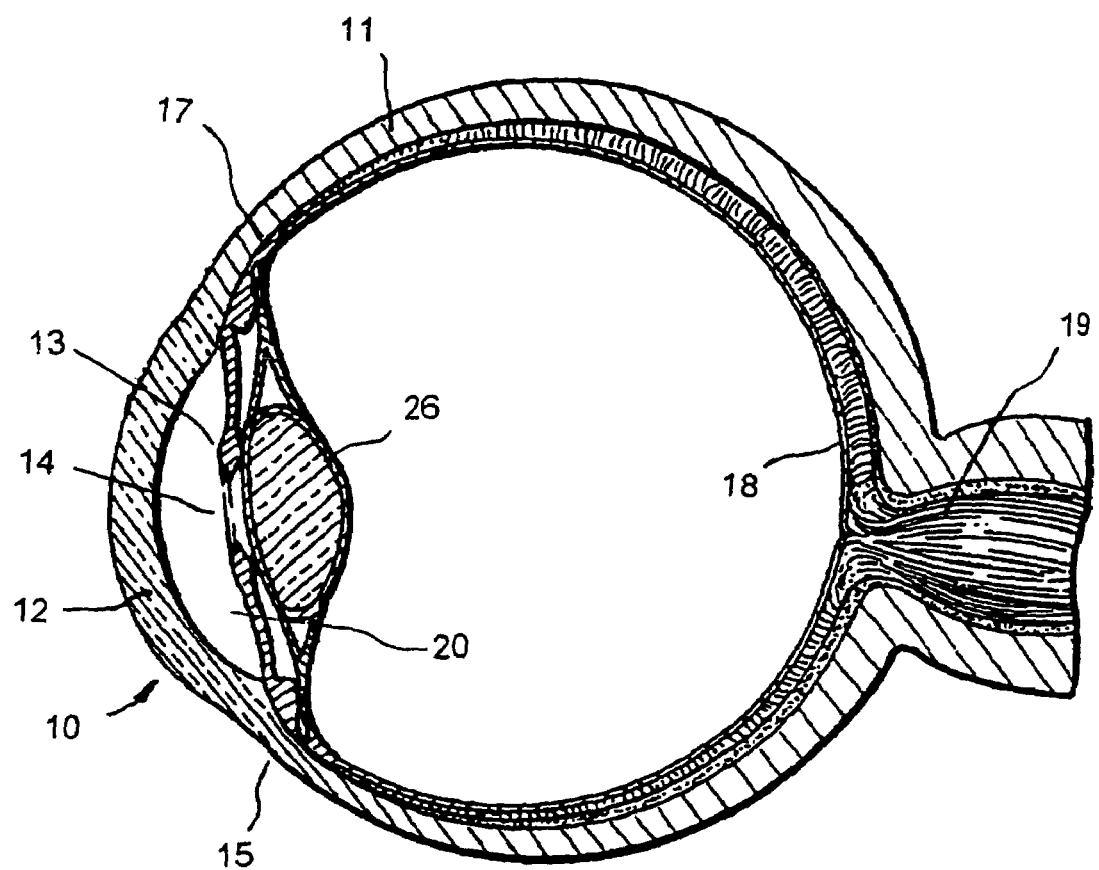
FIG. 1 is a sectional view of an eye for illustration purposes.
Figure 2:
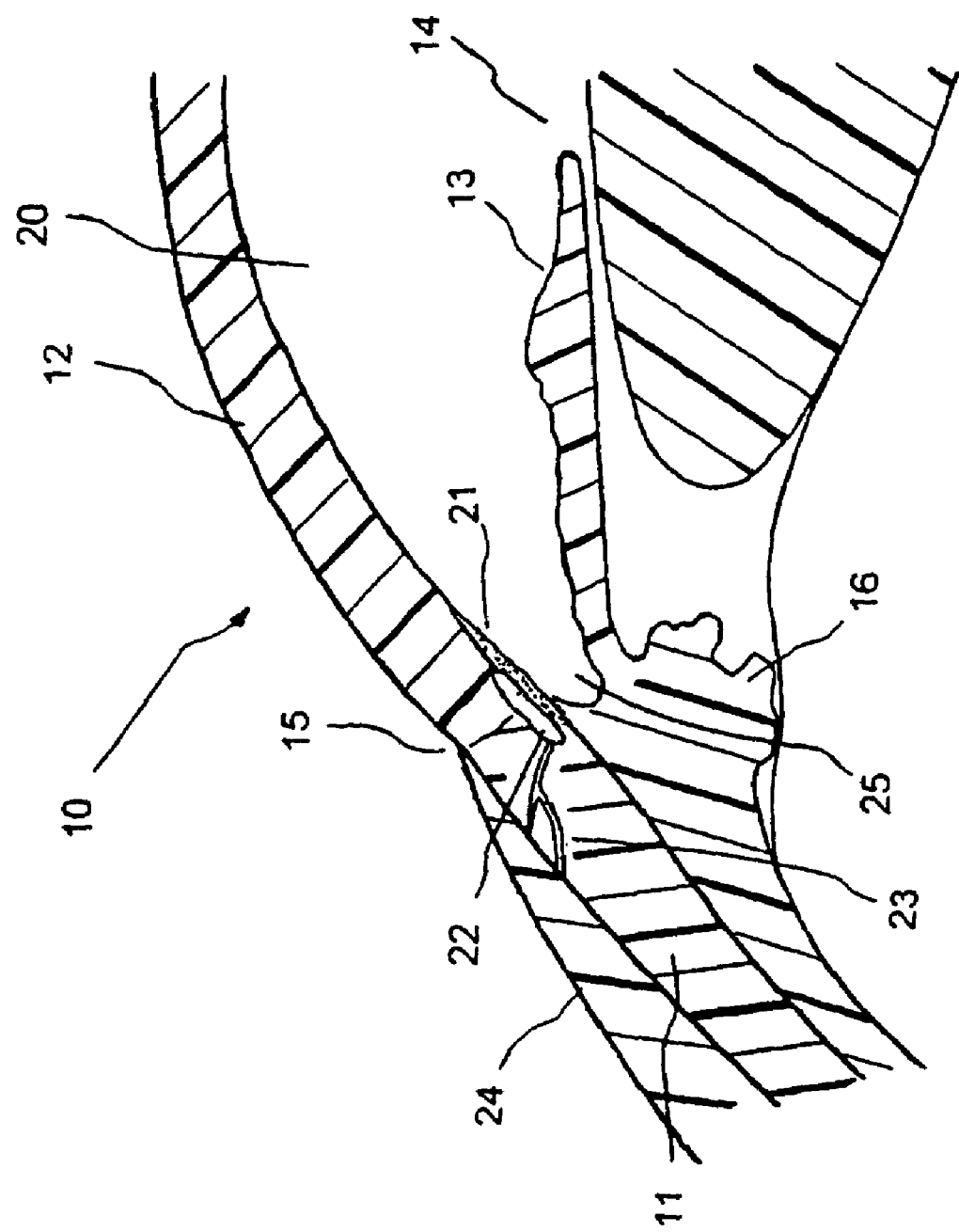
FIG. 2 is a close-up sectional view, showing the anatomical diagram of trabecular meshwork and the anterior chamber of the eye.

For background illustration purposes, FIG. 1 shows a sectional view of an eye 10, while FIG. 2 shows a close-up view, showing the relative anatomical locations of the trabecular meshwork, the anterior chamber, and Schlemm's canal. Thick collagenous tissue known as sclera 11 covers the entire eye 10 except that portion covered by the cornea 12. The cornea 12 is a thin transparent tissue that focuses and transmits light into the eye and the pupil 14, which is the circular hole in the center of the iris 13 (colored portion of the eye). The cornea 12 merges into the sclera 11 at a juncture referred to as the limbus 15. The ciliary body 16 begins internally in the eye and extends along the interior of the sclera 11 and becomes the choroid 17. The choroid 17 is a vascular layer of the eye underlying retina 18. The optic nerve 19 transmits visual information to the brain and is sequentially destroyed by glaucoma.

The anterior chamber 20 of the eye 10, which is bound anteriorly by the cornea 12 and posteriorly by the iris 13 and lens 26, is filled with aqueous. Aqueous is produced primarily by the ciliary body 16 and reaches the anterior chamber angle 25 formed between the iris 13 and the cornea 12 through the pupil 14. In a normal eye, the aqueous is removed through the trabecular meshwork 21. Aqueous passes through trabecular meshwork 21 into Schlemm's canal 22 and through the aqueous veins 23, which merge with blood-carrying veins, and into venous circulation. Intraocular pressure of the eye 10 is maintained by the intricate balance of secretion and outflow of the aqueous in the manner described above. Glaucoma is characterized by the excessive buildup of aqueous fluid in the anterior chamber 20, which produces an increase in intraocular pressure (fluids are relatively incompressible and pressure is directed equally to all areas of the eye).

As shown in FIG. 2, the trabecular meshwork 21 constitutes a small portion of the sclera 11. It is understandable that creating a hole or opening for implanting a device through the tissues of the conjunctiva 24 and sclera 11 is relatively a major surgery as compared to a surgery for implanting a device through the trabecular meshwork 21 only.

Figure 3:
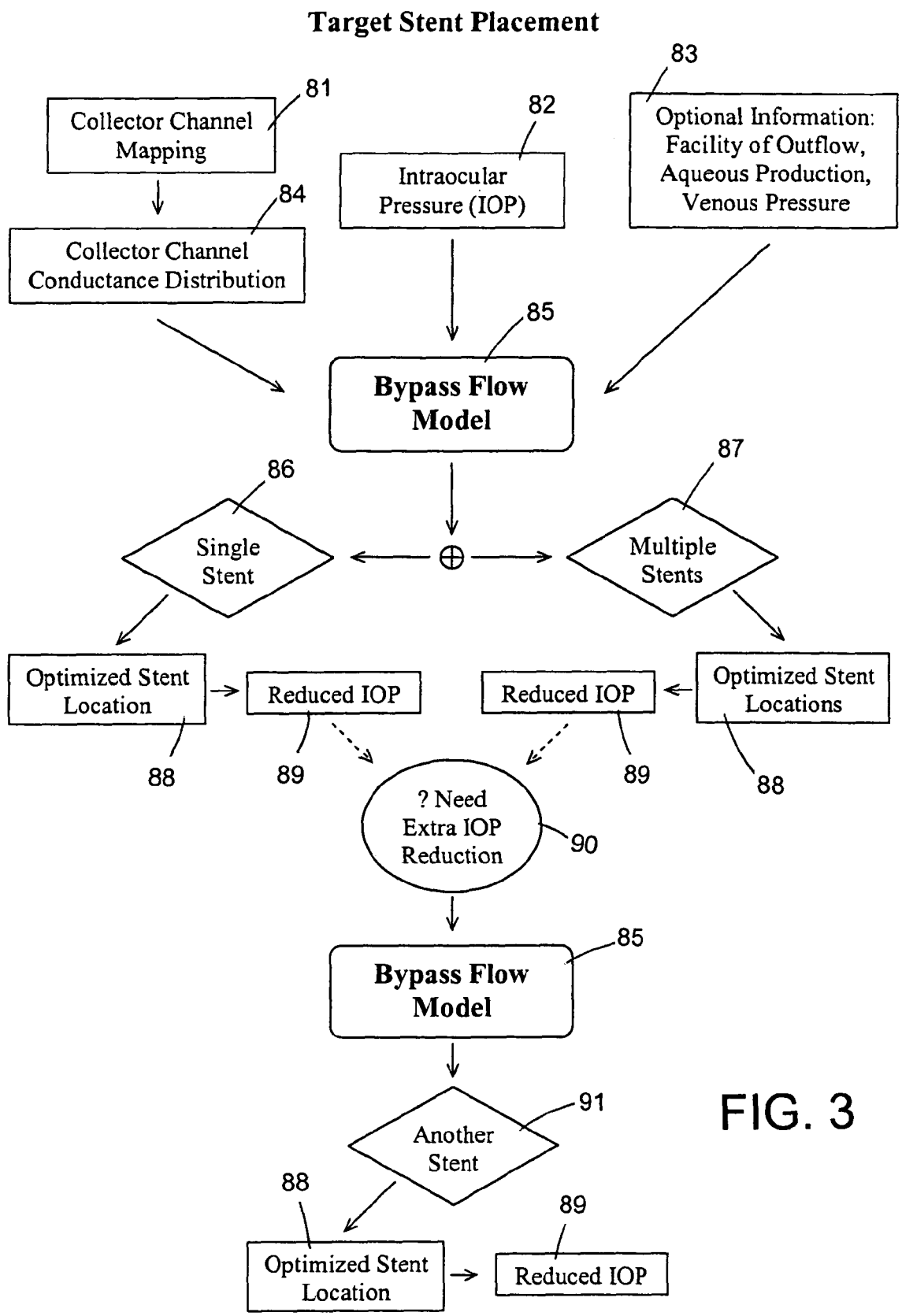
FIG. 3 is a flow diagram illustrating a method for treating glaucoma
Figure 4:
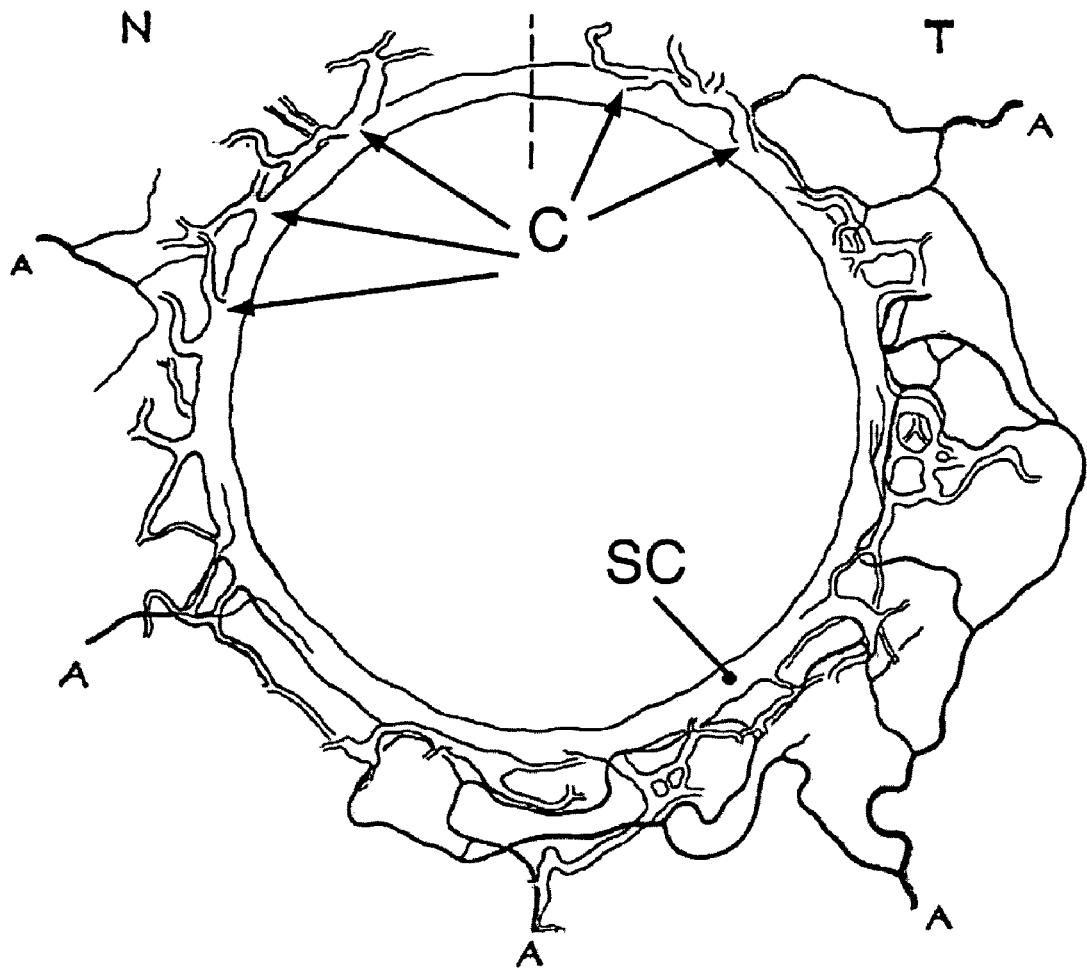
FIG. 4 is a sketch of Schlemm's canal, collector channels, and arteries.

FIG. 3 shows a flow diagram illustrating a decision tree for determining desired stent placement. In the illustrated embodiment, after it is determined that a patient is suffering from excess of intraocular pressure (IOP) 82, a bypass flow model 85 is determined to aid in the decision of whether or not to use a single stent 86 or multiple stents 87 at an optimized stent location(s) 88 resulting in reduced IOP 89. Optionally, the configuration of collector channels from collector channel mapping 81 in the patient's eye can be used to calculate collector channel conductance distribution 84 and to aid in the creation of a bypass flow model 85. Further, other information can be used, such as, for example, but without limitation, facility of outflow resistance, aqueous production, and venous pressure 83. After a first stent implantation, the patient is assessed again to see if extra IOP reduction 90 is needed. If the answer is yes by a physician, then another stent 91 is warranted at an optimized stent location 88 enabling reduced IOP 89.

By way of example, several cases of IOP reduction using the bypass flow model 85 of the invention are illustrated below. The IOP numbers are part of the data base shown in FIGS. 7–17.

Example No. 1

This example illustrates an IOP simulation for a normal individual, "uniform" outflow, and episcleral venous pressure of 10 mmHg. The input conditions comprise an episcleral venous pressure of about 10 mmHg, an aqueous production rate of about 2.4 μl/min, a trabecular meshwork resistance of about 1.25 mmHg/(μl/min), a collector channel resistance of about 1.25 mmHg/(μl/min) that is assumed uniformly distributed in this simulation, a Schlemm's canal resistance of about 1.0 mmHg/(μl/min)/mm, a Schlemm's canal circumferential length of about 36 mm, an aqueous humor viscosity of about 0.72 cP, and Schlemm's canal having a substantially elliptic cross section with a height of about 20 μm and a width of about 230 μm. From the bypass flow model, it is determined that this patient has an outflow facility of about 0.4 μl/min/mmHg and an intraocular pressure of about 16 mmHg.

Example No. 2

This example illustrates an IOP simulation for a normal individual, "uniform" outflow, and episcleral venous pressure of 9 mmHg. The input conditions comprise an episcleral venous pressure of about 9 mmHg, an aqueous production rate of about 2.4 μl/min, a trabecular meshwork resistance of about 1.25 mmHg/(μl/min), a collector channel resistance of about 1.25 mmHg/(μl/min) that is assumed uniformly distributed, a Schlemm's canal resistance of about 1.0 mmHg/(μl/min)/mm, a Schlemm's canal circumferential length of about 36 mm, an aqueous humor viscosity of about 0.72 cP, and Schlemm's canal having a substantially elliptic cross section with a height of about 20 μm and a width of about 230 μm. From the bypass flow model, it is determined that this patient has an outflow facility of about 0.4 μl/min/mmHg and an intraocular pressure of about 15 mmHg.

Example No. 3

This example illustrates an IOP simulation for a normal individual, "uniform" outflow, with bi-directional bypass. The input conditions comprise an episcleral venous pressure of about 9 mmHg, an aqueous production rate of about 2.4 μl/min, a trabecular meshwork resistance of about 1.25 mmHg/(μl/min), a collector channel resistance of about 1.25 mmHg/(μl/min) that is assumed uniformly distributed, a Schlemm's canal resistance of about 1.0 mmHg/(μl/min)/mm, a Schlemm's canal circumferential length of about 36 mm, an aqueous humor viscosity of about 0.72 cP, and Schlemm's canal having a substantially elliptic cross section with a height of about 20 μm and a width of about 230 μm, and a bi-directional bypass through the trabecular meshwork. From the bypass flow model, it is determined that this patient has an outflow facility of about 0.51 μl/min/mmHg and an intraocular pressure of about 13.8 mmHg.

Example No. 4

This example illustrates an IOP simulation for an individual with elevated IOP of 25 mmHg, "uniform" outflow and no stent implantation. The input conditions comprise an episcleral venous pressure of about 9 mmHg, an aqueous production rate of about 2.4 μl/min, a trabecular meshwork resistance of about 5.42 mmHg/(μl/min), a collector channel resistance of about 1.25 mmHg/(μl/min) that is assumed uniformly distributed, a Schlemm's canal resistance of about 1.0 mmHg/(μl/min)/mm, a Schlemm's canal circumferential length of about 36 mm, an aqueous humor viscosity of about 0.72 cP, and Schlemm's canal having a substantially elliptic cross section with a height of about 20 μm and a width of about 230 μm, From the bypass flow model, it is determined that this patient has an outflow facility of about 0.15 μl/min/mmHg and an intraocular pressure of about 25 mmHg.

Example No. 5

This example illustrates an IOP simulation for an individual with elevated IOP of 25 mmHg, "uniform" outflow and unidirectional bypass. The input conditions comprise an episcleral venous pressure of about 9 mmHg, an aqueous production rate of about 2.4 μl/min, a trabecular meshwork resistance of about 5.42 mmHg/(μl/min), a collector channel resistance of about 1.25 mmHg/(μl/min) that is assumed uniformly distributed, a Schlemm's canal resistance of about 1.0 mmHg/(μl/min)/mm, a Schlemm's canal circumferential length of about 36 mm, an aqueous humor viscosity of about 0.72 cP, and Schlemm's canal having a substantially elliptic cross section with a height of about 20 μm and a width of about 230 μm, and a unidirectional bypass through the trabecular meshwork. From the bypass flow model, it is determined that this patient has an outflow facility of about 0.26 μl/min/mmHg and an intraocular pressure of about 18.3 mmHg.

Example No. 6

This example illustrates an IOP simulation for an individual with elevated IOP of 25 mmHg, "uniform" outflow, and bi-directional bypass. The input conditions comprise an episcleral venous pressure of about 9 mmHg, an aqueous production rate of about 2.4 μl/min, a trabecular meshwork resistance of about 5.42 mmHg/(μl/min), a collector channel resistance of about 1.25 mmHg/(μl/min) that is assumed uniformly distributed, a Schlemm's canal resistance of about 1.0 mmHg/(μl/min)/mm, a Schlemm's canal circumferential length of about 36 mm, an aqueous humor viscosity of about 0.72 cP, and Schlemm's canal having a substantially elliptic cross section with a height of about 20 μm and a width of about 230 μm, and a bi-directional bypass through the trabecular meshwork. From the bypass flow model, it is determined that this patient has an outflow facility of about 0.37 μl/min/mmHg and an intraocular pressure of about 15.5 mmHg.

Example No. 7

This example illustrates an IOP simulation for an individual with elevated IOP of 25 mmHg, "uniform" outflow, unidirectional bypass, and unidirectional 20-μm canal dilation. The input conditions comprise an episcleral venous pressure of about 9 mmHg, an aqueous production rate of about 2.4 μl/min, a trabecular meshwork resistance of about 5.42 mmHg/(μl/min), a collector channel resistance of about 1.25 mmHg/(μl/min) that is assumed uniformly distributed, a Schlemm's canal resistance of about 1.0 mmHg/(μl/min)/mm, a Schlemm's canal circumferential length of about 36 mm, an aqueous humor viscosity of about 0.72 cP, and Schlemm's canal having a substantially elliptic cross section with a height of about 20 μm and a width of about 230 μm, with a unidirectional bypass through the trabecular meshwork and a unidirectional dilation of Schlemm's canal with a maximum height of 30 μm that decreases linearly to 20 μm over a 9 mm circumferential length of Schlemm's canal. From the bypass flow model, it is determined that his patient has an outflow facility of about 0.35 μl/min/mmHg and an intraocular pressure of about 15.9 mmHg.

Example No. 8

This example illustrates an IOP simulation for an individual with elevated IOP of 25 mmHg, "uniform" outflow, bi-directional bypass, and bi-directional 30 μm canal dilation. The input conditions comprise an episcleral venous pressure of about 9 mmHg, an aqueous production rate of about 2.4 μl/min, a trabecular meshwork resistance of about 5.42 mmHg/(μl/min), a collector channel resistance of about 1.25 mmHg/(μl/min) that is assumed uniformly distributed, a Schlemm's canal resistance of about 1.0 mmHg/(μl/min)/mm, a Schlemm's canal circumferential length of about 36 mm, an aqueous humor viscosity of about 0.72 cP, and Schlemm's canal having a substantially elliptic cross section with a height of about 20 μm and a width of about 230 μm, with a bi-directional bypass through the trabecular meshwork and a bi-directional dilation of Schlemm's canal with a maximum height of 30 μm that decreases linearly to 20 μm over a 9 mm circumferential length of Schlemm's canal (in each direction). From the bypass flow model, it is determined that this patient has an outflow facility of about 0.52 μl/min/mmHg and an intraocular pressure of about 13.6 mmHg.

Example No. 9

This example illustrates an IOP simulation for an individual with elevated IOP of 34 mmHg, "average-eye" outflow, and bi-directional bypass at a non-optimized outflow point. The "average-eye" outflow follows the calculated data as shown on FIG. 18. The input conditions comprise an episcleral venous pressure of about 10 mmHg, an aqueous production rate of about 2.4 µl/min, a trabecular meshwork resistance of about 8.75 mmHg/(µl/min), a collector channel resistance of about 1.25 mmHg/(µl/min) that is assumed distributed according to an average distribution of outflow collector channels, a Schlemm's canal resistance of about 1.0 mmHg/(µl/min)/mm, a Schlemm's canal circumferential length of about 36 mm, an aqueous humor viscosity of about 0.72 cP, and Schlemm's canal having a substantially elliptic cross section with a height of about 20 µm and a width of about 230 µm, with a bi-directional bypass through the trabecular meshwork located at a non-optimal location where localized collector channel outflow resistance is highest. From the bypass flow model, it is determined that this patient has an outflow facility of about 0.29 µl/min/mmHg and an intraocular pressure of about 18.4 mmHg.

Example No. 10

This example illustrates an IOP simulation for an individual with elevated IOP of 34 mmHg, "average-eye" outflow, and bi-directional bypass at an optimized outflow point. The input conditions comprise an episcleral venous pressure of about 10 mmHg, an aqueous production rate of about 2.4 µl/min, a trabecular meshwork resistance of about 8.75 mmHg/(µl/min), a collector channel resistance of about 1.25 mmHg/(µl/min) that is assumed distributed according to an average distribution of outflow collector channels, a Schlemm's canal resistance of about 1.0 mmHg/(µl/min)/mm, a Schlemm's canal circumferential length of about 36 mm, an aqueous humor viscosity of about 0.72 cP, and Schlemm's canal having a substantially elliptic cross section with a height of about 20 µm and a width of about 230 µm, with a bi-directional bypass through the trabecular meshwork located at an optimal location where localized collector channel outflow resistance is lowest. From the bypass flow model, it is determined that this patient has an outflow facility of about 0.41 µl/min/mmHg and an intraocular pressure of about 15.8 mmHg.

Example No. 11

This example illustrates an IOP simulation for an individual with elevated IOP of 34 mmHg, "average-eye" outflow, and two bi-directional bypasses at optimized outflow points. The input conditions comprise an episcleral venous pressure of about 10 mmHg, an aqueous production rate of about 2.4 µl/min, a trabecular meshwork resistance of about 8.75 mmHg/(µl/min), a collector channel resistance of about 1.25 mmHg/(µl/min) that is assumed distributed according to an average distribution of outflow collector channels, a Schlemm's canal resistance of about 1.0 mmHg/(µl/min)/mm, a Schlemm's canal circumferential length of about 36 mm, an aqueous humor viscosity of about 0.72 cP, and Schlemm's canal having a substantially elliptic cross section with a height of about 20 µm and a width of about 230 µm, with two bi-directional bypasses through the trabecular meshwork each located at an optimal location where localized collector channel outflow resistance is lowest. From the bypass flow model, it is determined that this patient has an outflow facility of about 0.67 µl/min/mmHg and an intraocular pressure of about 13.6 mmHg.

Example No. 12

This example illustrates an IOP simulation for an individual with elevated IOP of 34 mmHg, "specific-eye" outflow, and two bi-directional bypasses at optimized outflow points. The input conditions comprise an episcleral venous pressure of about 10 mmHg, an aqueous production rate of about 2.4 µl/min, a trabecular meshwork resistance of about 8.75 mmHg/(µl/min), a collector channel resistance of about 1.25 mmHg/(µl/min) that is assumed distributed according to a specific individualized distribution of outflow collector channels, a Schlemm's canal resistance of about 1.0 mmHg/(µl/min)/mm, a Schlemm's canal circumferential length of about 36 mm, an aqueous humor viscosity of about 0.72 cP, and Schlemm's canal having a substantially elliptic cross section with a height of about 20 µm and a width of about 239 µm, with two bi-directional bypasses through the trabecular meshwork each located at an optimal location where localized collector channel outflow resistance is lowest. From the bypass flow model, it is determined that this patient has an outflow facility of about 0.6 to 0.7 µl/min/mmHg and an intraocular pressure of about 14.0 to 13.4 mmHg. For a "specific-eye" outflow that deviates from the "average-eye" outflow, this example illustrates that the bypass flow model is capable of reducing the IOP to a desired level when stents are implanted at about the optimal location where localized collector channel outflow resistance is lowest.

The trabecular bypass flow model, which can be based on the above-noted information, is determined so as to provide a desired strategy for lowering the excessive intraocular pressure. If it is decided that a single stent should be used, an optimized stent location is first determined based on the bypass flow model. The implantation of the single stent results in reduced IOP. After this implantation, it is again determined if there is a need for further reduction in IOP. If additional IOP reduction is desired, then a further bypass flow model is created. For example, the second bypass flow model can be determined in the same or similar manner as the first bypass flow model described above. In light of the second bypass flow model, an additional stent can be implanted at an optimized location to further reduce IOP.

If it is determined, in light of the first bypass flow model, that multiple stents should be used, the location of the multiple stents is first optimized. Then, the multiple stents are implanted. Afterwards, it is again determined if additional intraocular pressure reduction is needed, and the decision or recommendation can continue as noted above.

Where additional stents are implanted in light of the second bypass flow model, the additional stents can be different from the first stents implanted. For example, where a single or multiple stents are implanted in accordance with the first bypass flow model, the additional stents can be of a different type. For example, in one embodiment, the second stent is the same as the first stent. In another embodiment, the second stent(s) is injectable or axisymmetric stent. In still another embodiment, the second stent(s) is smaller than (in some cases, larger than) the first stent. The dose response may also relate to the stent configuration or characteristics such as drug-loading or surface treatment enabling enhancing aqueous transport or therapeutic effects on the tissue as needed.

A stent is placed into Schlemm's canal to provide a patent channel of aqueous communication between the anterior chamber and the lumen of Schlemm's canal and/or subsequent anatomical aspects of the physiological outflow system of the eye by an ab interno or ab externo procedure. Some aspects of the invention provide the concepts of targeted stent placement and multi-stent therapy and provide evidence, in the form of compiled and analyzed microanatomy findings and numerical modeling of the outflow system of the human eye, for their expected efficacy.

Aqueous humor is produced in the ciliary body (~2 μl/min) and flows up through the pupil and out through the trabecular meshwork into Schlemm's canal; subsequently, the fluid exits the canal through small (canal outlets) collector channels (generally fewer than 30 in number in an eye) to the episcleral venous system. The episcleral venous system consists of small veins of the eye, some of which are filled, or partially filled, with aqueous. Aqueous-filled, partially aqueous-filled, occasionally aqueous-filled, or occasionally partially aqueous-filled episcleral veins are usually referred to as aqueous veins.

Some aspects of the invention relate to means for identifying the number and size of the collector channels (or the sum of the aqueous outflow quantity at each region of the canal circumference) at the vicinity of Schlemm's canal enabling targeting and implanting a single stent or a plurality of glaucoma stents for optimally treating elevated intraocular pressure. By way of example, the reflux of blood toward Schlemm's canal can be tracked dynamically using a slip lamp when a patient's head is turned from a bowing position to an upright position.

Targeted Placement

Targeted placement refers to the intentional placement of a stent at a particular location in Schlemm's canal for the purpose of providing a maximum benefit in the form of maximum outflow facility. The micro-anatomy of Schlemm's canal, determined from neoprene castings, is shown in schematic form in FIG. 4 for the purpose of this discussion.

Figure 19:
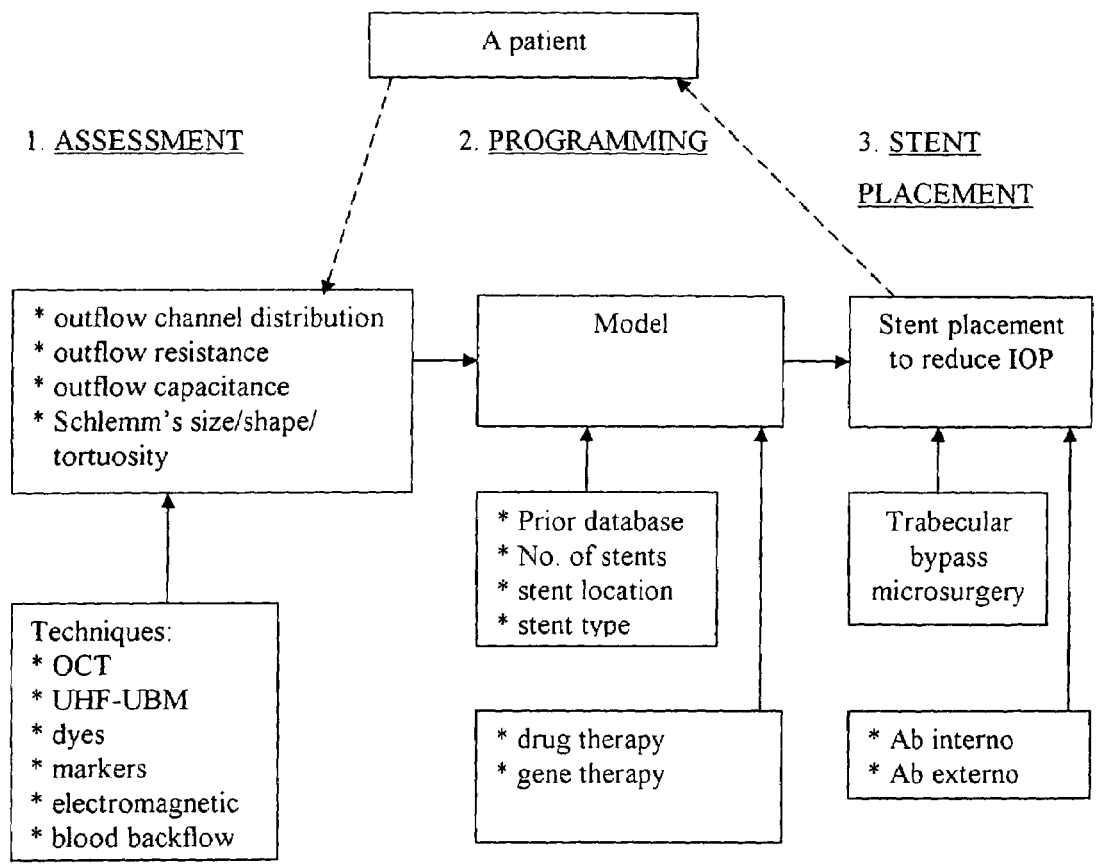
FIG. 19 is a schematic diagram for programming stent placement according to the principles of the present invention.

Programmed (also known as "Targeted") placement refers to the intentional placement of a stent at a particular location or locations in Schlemm's canal for the purpose of providing a maximum benefit in the form of maximum outflow facility. In some aspect of the present invention, a method is provided of assessing the outflow characteristics (outflow channel distribution around Schlemm's canal, outflow resistance, outflow capacitance, Schlemm's canal shape/size/tortuosity at various locations or regions, and other factors) of a patient around the eye, determining a most effective stent placement program, and implanting the stent(s) in one or plurality of procedures at the programmed location(s). The most effective stent placement program may comprise several factors including prior database, number of stents, each stent location, type of stent, and associated drug therapy. FIG. 19 shows a schematic diagram for programming stent placement according to the principles of the present invention.

Aqueous enters Schlemm's canal through the trabecular meshwork and travels along the canal to exit through the collector channels. Schlemm's canal is a narrow channel with approximate dimensions of 250 um×20 um with a 40 mm length (Volume ~0.2 μl) and it provides measurable resistance to the flow of aqueous. Therefore, placing a stent into Schlemm's canal through the trabecular meshwork yields the best improvement in outflow facility when it is placed near a large collector channel or a group of smaller ones that combine to have a larger equivalent hydraulic diameter. Numerical modeling of the outflow system of the eye provides essential information to determine the best implant location based on the collector channel distribution and size. Collector duct locations and sizes are determined from micro-anatomical studies or by real-time imaging. Further details regarding the spatial distribution and size of the collector channels and the numerical model are provided latter in this disclosure.

Experimental evidence has demonstrated that the trabecular meshwork is the site of increased outflow resistance that reduces facility of outflow and elevates intraocular pressure (IOP) in human eyes with primary open angle glaucoma. Laser trabeculoplasty procedures, aimed at reducing the outflow resistance of trabecular meshwork, have been successful in lowering the IOP in glaucomatous eyes. Partial trabeculotomies appear to be effective in enhancing the facility of outflow in enucleated normal and glaucomatous human eyes. In theory, twenty holes of 10 μm in diameter in trabecular meshwork were adequate to bypass the entire resistance of the meshwork. Laser trabecular ablation has been utilized to produce a number of openings in the trabecular meshwork to reduce IOP. Devices such as a silicone tube, a Y-shaped shunt, and a trabecular bypass stent, which provide a single passageway between the anterior chamber and the Schlemm's canal, have been recently developed and implanted into glaucoma patients.

Viscocanalostomy is a nonpenetrating glaucoma surgical procedure where Schlemm's canal is unroofed by excising a deep sclera flap, a Descemet's window is created, and the canal is expanded by injection of visoelastic. Reportedly, the aqueous humor percolates through the trabecular meshwork, enters the scleral lake, travels circumferentially in the newly dilated Schlemm's canal, and reaches the collector channel ostia and ultimately the aqueous and episcleral veins. The dramatically reduced resistance in the outflow pathway results in a lowered IOP. Histological data has revealed that the dimensions of Schlemm's canal after cannulation and viscoelastic injection are markedly enlarged at and up to 16 mm downstream of the insertion point of the cannula.

In a current study, an outflow model has been developed to investigate the mechanism of action of a trabecular bypass, a patent passageway constructed through the trabecular meshwork. It is theoretically demonstrated that a single trabecular bypass in a glaucomatous eye was able to enhance the facility of outflow and reduce the IOP to physiological levels. The resistance of Schlemm's canal to circumferential flow plays a critical role in determining how effective a trabecular bypass can be on IOP reduction. The present study also explores the impact of Schlemm's canal and collector channel dilation in the vicinity of a patent trabecular bypass on the enhancement of IOP reduction.

Flow Model

In the presence of a bypass in trabecular meshwork, the main portion of the aqueous humor enters Schlemm's canal via the bypass and the remaining portion via the trabecular meshwork. The aqueous humor travels circumferentially in Schlemm's canal and is drained by collector channels to aqueous and episcleral veins. As a theoretical approach, the collector channels are assumed to be close enough and equally spaced to form a uniform leaking structure with a total resistance of $R_{CC}$ to outflow. The total resistance of the trabecular meshwork to outflow is designated $R_{TM}$. The intraocular pressure in the anterior chamber is designated $P_I$ and the venous pressure at the end of the collector channels $P_V$. At a circumferential distance x from where Schlemm's canal is exposed to the bypass, the pressure, the circumferential flow, and the circumferential flow resistance per unit length in Schlemm's canal, are designated p(x), f(x), and $R_{SC}(x)$, respectively. The following two equations govern the pressure and flow in Schlemm's canal.

$$\frac{dp}{dx} = -R_{SC} f \qquad (1)$$

$$\frac{df}{dx} = \frac{P_I - p}{LR_{TM}} - \frac{p - P_V}{LR_{CC}} = -\left(\frac{1}{LR_{TM}} + \frac{1}{LR_{CC}}\right)p + \left(\frac{P_I}{LR_{TM}} + \frac{P_V}{LR_{CC}}\right) \qquad (2)$$

where L is the circumference of Schlemm's canal. These two first order linear ordinary differential equations can be uniquely solved with two boundary conditions.

A unidirectional trabecular bypass is constructed to allow the aqueous humor entering Schlemm's canal to flow in only one direction while the flow in the opposite direction is blocked. Thus, the canal is exposed to the anterior chamber at x=0 and the circumferential flow is zero, at x=L. The two boundary conditions for this case are $$p = P_I \text{ at } x=0 \text{ and } f=0 \text{ at } x=L \qquad (3a)$$

A bidirectional trabecular bypass is constructed to allow aqueous humor to directly enter Schlemm's canal and flow in both directions. The two boundary conditions for this case are $$p = P_I \text{ at } x=0 \text{ and at } x=L \qquad (3b)$$

If Schlemm's canal is uniformly shaped with a constant resistance $R_{SC}$ to circumferential flow, the equations (1) and (2) can be solved analytically with two given boundary conditions (3a) or (3b), as obvious in the current study. However, if Schlemm's canal is not uniform and therefore has a spatially varying resistance, a numerical method has to be applied to solve equations (1) and (2).

Once p(x) is derived, the flow through trabecular meshwork, $F_{TM}$, can be calculated, $$F_{TM} = \int_0^L \frac{P_I - p}{R_{TM}} \frac{dx}{L} \qquad (4)$$

as well as the outflow through the collector channels, $F_{CC}$, i.e. the total outflow, $$F_{CC} = \int_0^L \frac{p - P_V}{R_{CC}} \frac{dx}{L} \qquad (5)$$

The flow through the trabecular bypass, $F_{BP}$, is the difference between $F_{CC}$ and $F_{TM}$.

$$F_{BP} = F_{CC} - F_{TM} \qquad (6)$$

The facility of outflow, C, is defined as $$C = \frac{F_{CC}}{P_I - P_V} \qquad (7)$$

Moses (Am J Ophthalmol 1979; 88:585–591) modeled Schlemm's canal as an elliptical tube to study the circumferential flow between two collector channels. The resistance of the elliptical tube per unit length to circumferential flow, $R_{SC}$, can be written.

$$R_{SC} = \frac{4\mu\left[\left(\frac{h}{2}\right)^2 + \left(\frac{w}{2}\right)^2\right]}{\pi\left(\frac{h}{2}\right)^3 \left(\frac{w}{2}\right)^3} \qquad (8)$$

where $\mu$ is the viscosity of the aqueous humor, h the canal height (the minor diameter of the ellipse), and w the canal width (the major diameter of the ellipse).

Smit and Johnstone (Ophthalmology 2002; 109:786–792) studied the effect of viscoelastic injection on the dimensions of Schlemm's canal in human eyes and found that the height of Schlemm's canal increased by 10 fold at the site of cannula insertion and Schlemm's canal was measurably dilated 6 to 14 mm beyond the cannula tip. The relationship between the height of Schlemm's canal and the distance along Schlemm's canal beyond the cannula tip can be fitted nicely with a simple linear regression. The change in width of Schlemm's canal was much smaller than that in height. A marked dilation of collector channel ostia and associated collector channels was also observed.

Figure 5:
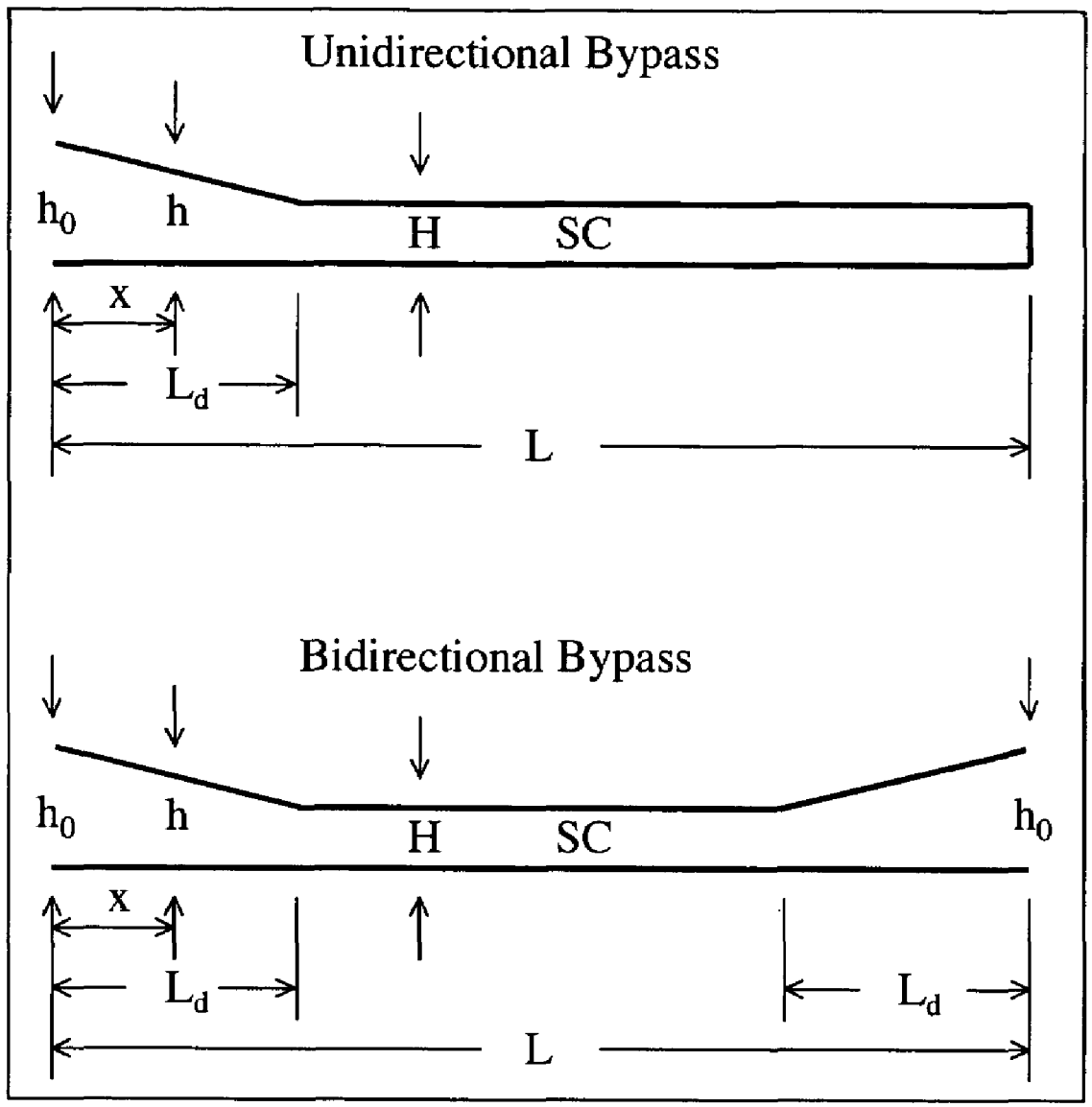
FIG. 5 is a schematic drawing of the dilated Schlemm's canal.

If Schlemm's canal can be patently dilated with a viscoelastic material or by other means the same time a trabecular bypass is constructed, its dimension is enlarged and the canal resistance to circumferential flow is decreased. In this study, the change in canal height, more substantial than that in canal width, is considered as the sole factor to affect the canal resistance as described in equation (8). Designate H as the normal canal height before dilation, $h_0$ as the dilated canal height at the bypass, and $L_d$ as the circumferential length of the dilated portion of the canal. The canal height, h(x), at a circumferential distance x from the bypass, has a linear distribution over the dilated length of canal (FIG. 5).

$$h = h_0 - (h_0 - H)\frac{x}{L_d} \text{ at } 0 \leq x \leq L_d \text{ and } h = H \text{ at } L_d \leq x, \qquad (9a)$$

for a unidirectional bypass, and $$h = h_0 - (h_0 - H)\frac{x}{L_d} \text{ at } 0 \leq x \leq L_d, \qquad (9b)$$

$$h = H \text{ at } L_d \leq x \leq L - L_d, \text{ and}$$

$$h = h_0 - (h_0 - H)\frac{L-x}{L_d} \text{ at } L - L_d \leq x \leq L,$$

for a bidirectional bypass.

How the dilation of collector channels affects the outflow resistance in collector channels has not been previously quantified. However, the model is capable of taking into account any distribution function in collector channel resistance once it is quantitatively available. To illustrate the effect of collector channel dilation, it is assumed that the collector channel resistance, $r_{CC}(x)$, is a second order polynomial of x.

$$r_{CC} = r_{CC0} + (R_{CC} - r_{CC0})\left(\frac{x}{L_d}\right)^2 \text{ at } 0 \le x \le L_d, \text{ and} \quad (10a)$$

$$r_{CC} = R_{CC} \text{ at } L_d \le x,$$

for a unidirectional bypass, and $$r_{CC} = r_{CC0} + (R_{CC} - r_{CC0})\left(\frac{x}{L_d}\right)^2 \text{ at } 0 \le x \le L_d, \quad (10b)$$

$$r_{CC} = R_{CC} \text{ at } L_d \le x \le -L_d, \text{ and}$$

$$r_{CC} = r_{CC0} + (R_{CC} - r_{CC0})\left(\frac{L-x}{L_d}\right)^2 \text{ at } L - L_d \le x \le L,$$

for a bidirectional bypass, where $r_{CC0}$ is the equivalent total collector channel resistance at the bypass. When considering the collector channel dilation, $r_{CC}$ would replace $R_{CC}$ in equations (2) and (5).

A numerical method is developed to seek the solutions of equations (1) to (10) within the LabView (National Instruments, Austin, Tex.) programming environment, utilizing an improved Euler (predictor-corrector) method for solving ordinary differential equations and a bisection method for solving nonlinear equations. The reduced IOP is deduced with the constraint of a constant total outflow in equation (5).

Bypass Flow Model Simulation

In an average normal eye, the trabecular meshwork and the collector channels each represents 50% of the total outflow resistance, at about 1.25 mmHg/(μl/min). Moses et al. (Invest Ophthalmol Vis Sci 1981; 20:61–68) measured the resistance of Schlemm's canal to circumferential flow at various intraocular pressures; at a pressure difference ($P_I$–$P_V$) of 10 mmHg, it has a range from 0.32 to 1.42 mmHg/(μl/min) per millimeter of canal length. In the present model, the baseline canal resistance is conveniently chosen near the middle of this measured range at 1 mmHg/(μl/min)/mm. The typical height of Schlemm's canal is about 20 μm. From these values, the equivalent width of an elliptic shaped Schlemm's canal is about 230 μm according to equation (8), which corresponds reasonably well with the observed anatomical width. The average parameters for normal eyes are listed in a table of FIG. 6. In an eye with primary open angle glaucoma, the total conventional outflow and the collector channel resistance are assumed normal, but the resistance in trabecular meshwork is abnormally high, which results in an elevated IOP. Thus, a glaucomatous eye is represented with a higher value in $R_{TM}$ in the model.

Figure 7:
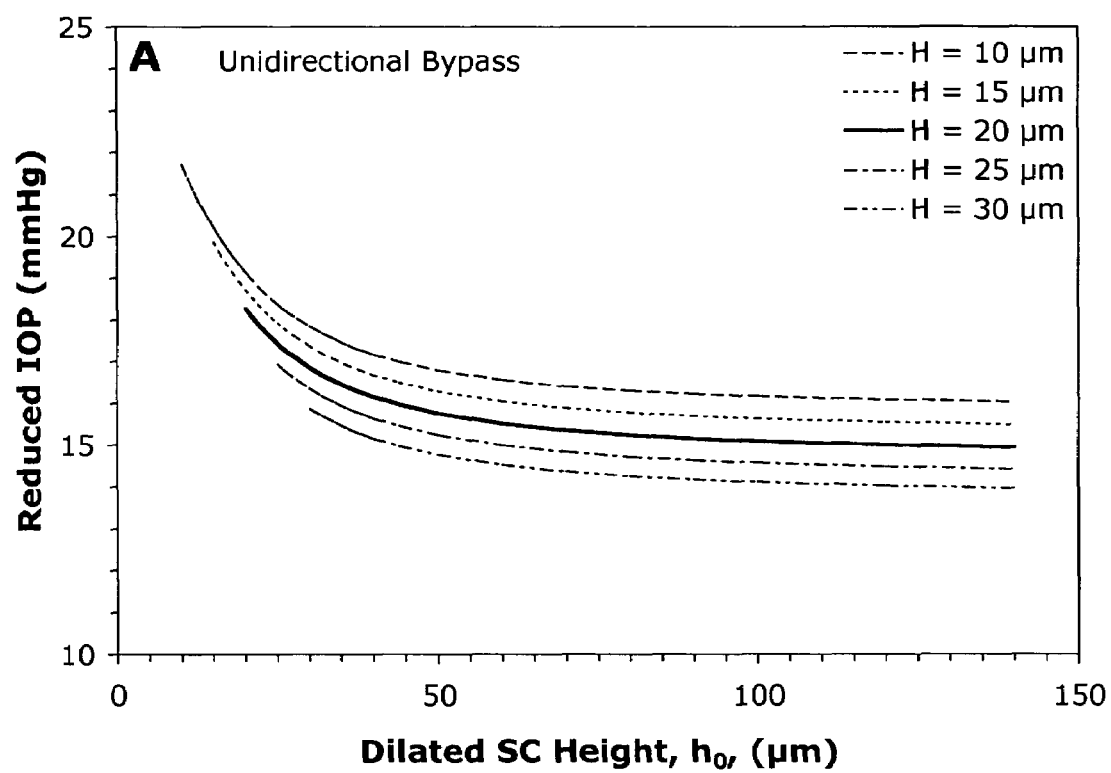
FIG. 7 shows the effect of Schlemm's canal dilation in the presence of (A) a unidirectional bypass on IOP reduction for five initial canal height of 10, 15, 20, 25, and 30 µm. The initial elevated IOP is 25 mmHg. The dilation of Schlemm's canal is limited to a quadrant from the bypass, i.e. $L_d = L/4$.
Figure 8:
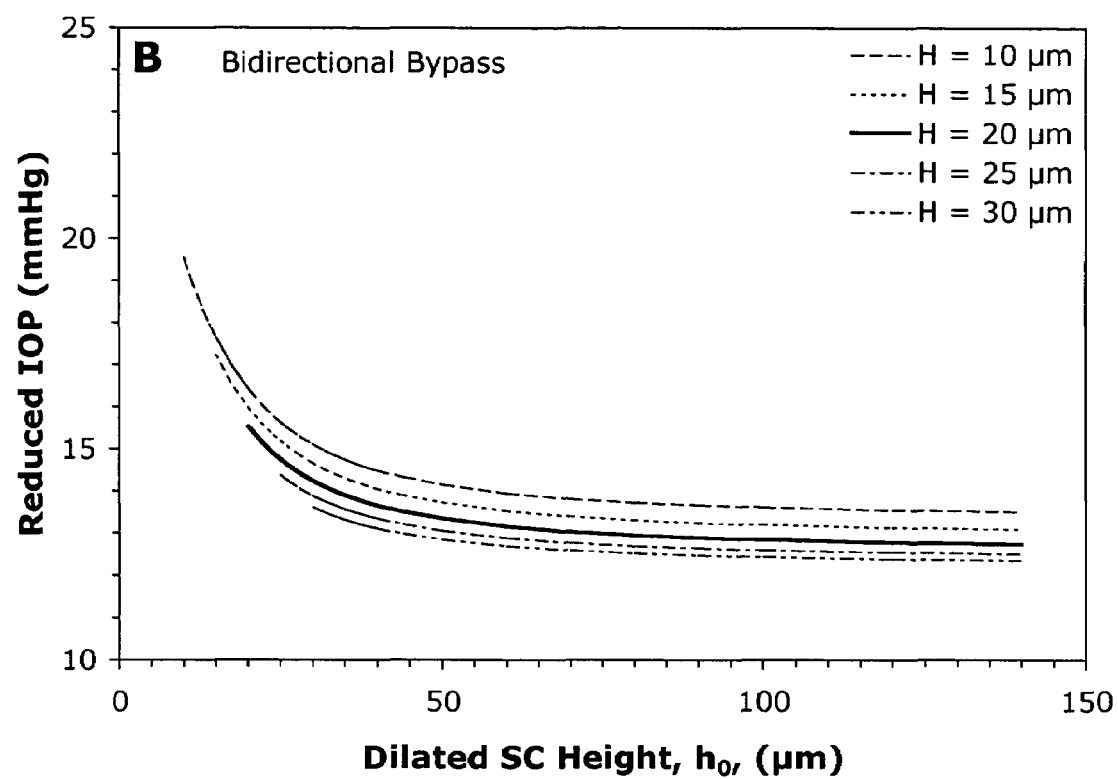
FIG. 8 shows the effect of Schlemm's canal dilation in the presence of (B) a bidirectional bypass on IOP reduction for five initial canal heights of 10, 15, 20, 25, and 30 µm. The initial elevated IOP is 25 mmHg. The dilation of Schlemm's canal is limited to a quadrant from the bypass, i.e. $L_d = L/4$.

The effect of Schlemm's canal dilation on IOP reduction is illustrated in FIG. 7 for the unidirectional trabecular bypass and FIG. 8 for the bidirectional trabecular bypass. The initial elevated IOP is taken at 25 mmHg, which would correspond to a trabecular meshwork resistance of 5.417 mmHg/(μl/min). Five sizes of Schlemm's canal with a different initial canal height of 10, 15, 20, 25, and 30 μm and the same canal width of 230 μm are considered in the calculation. The canal resistance at these five heights are 7.96, 2.36, 1.00, 0.51, and 0.30 mmHg/(μl/min)/mm, respectively, according to equation (8). The dilation of Schlemm's canal is limited to a quadrant from the bypass, i.e. $L_d$=L/4, which is comparable to that observed in the study by Smit and Johnstone. At these baseline height, the IOP is reduced to 21.7, 19.9, 18.3, 16.9, and 15.9 mmHg, respectively, in the presence of a unidirectional bypass, and to 19.6, 17.2, 15.5, 14.4, and 13.6 mmHg, respectively, in the presence of a bidirectional bypass. It is worth noting that these baseline canal heights have negligible impact on the IOP of patients without a trabecular bypass, since circumferential flow in Schlemm's canal is minute in the unaltered anatomy. As the canal expands, the IOP drops rapidly, especially for canal with a smaller initial height. The drop in IOP slows down when the canal height at the bypass is dilated to the 40~50 μm range. The IOP shows very little reduction as the canal further expands beyond 50 μm. When the canal height is expanded to 40 μm at the bypass, the IOP is reduced to 17.2, 16.7, 16.2, 15.6, and 15.2 mmHg, respectively, in the presence of a unidirectional bypass, and to 14.5, 14.1, 13.7, 13.3, and 13.1 mmHg, respectively, in the presence of a bidirectional bypass.

Figure 9:
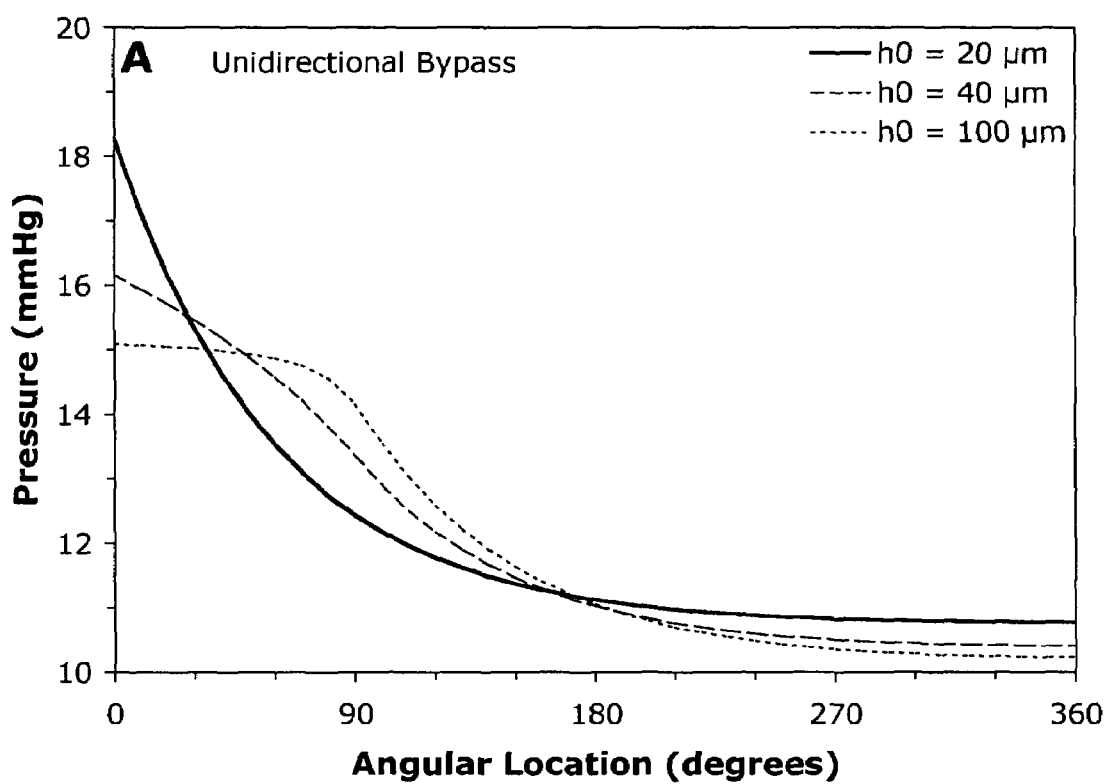
FIG. 9 shows pressure distribution in Schlemm's canal in the presence of (A) a unidirectional trabecular bypass, without canal dilation ($h_0 = 20$ µm) and with moderate ($h_0 = 40$ µm) and large ($h_0 = 100$ µm) canal dilation. The eye has an initial canal height of 20 µm and an initial elevated IOP of 25 mmHg. The dilation of the Schlemm's canal is limited to a quadrant from the bypass, i.e. $L_d = L/4$.
Figure 10:
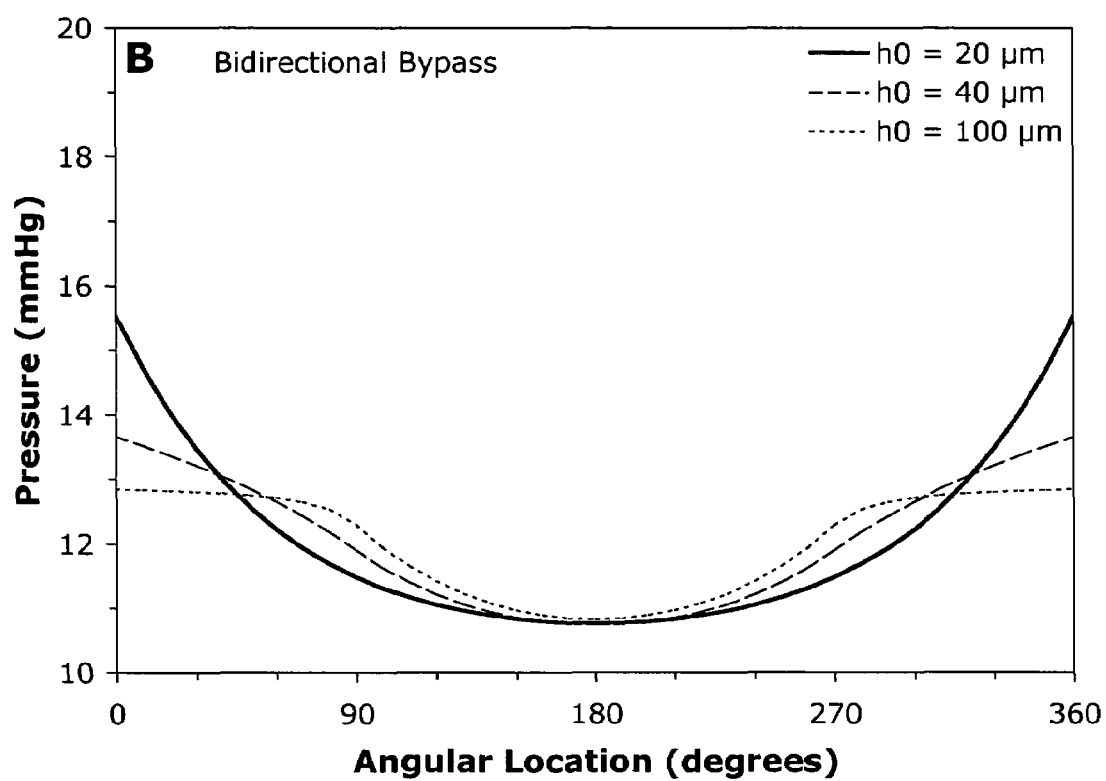
FIG. 10 shows pressure distribution in Schlemm's canal in the presence of (B) a bidirectional trabecular bypass, without canal dilation ($h_0 = 20$ µm) and with moderate ($h_0 = 40$ µm) and large ($h_0 = 100$ µm) canal dilation. The eye has an initial canal height of 20 µm and an initial elevated IOP of 25 mmHg. The dilation of the Schlemm's canal is limited to a quadrant from the bypass, i.e. $L_d = L/4$.
Figure 11:
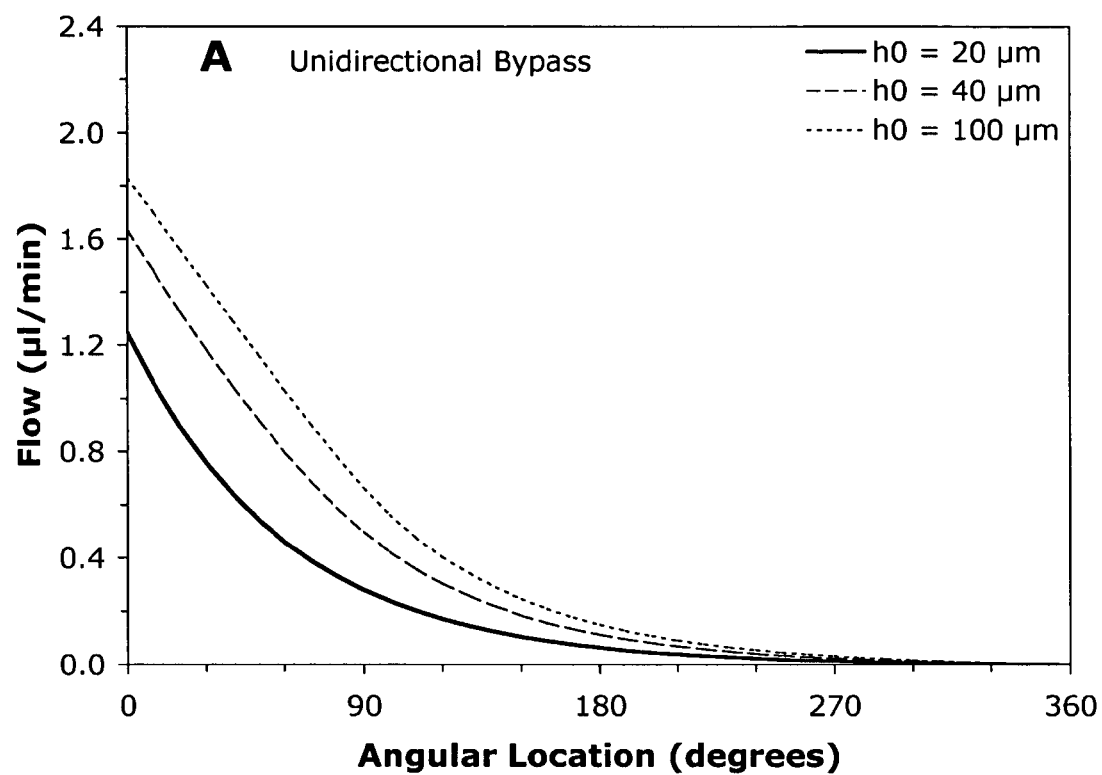
FIG. 11 shows circumferential flow distribution in Schlemm's canal in the presence of (A) a unidirectional trabecular bypass, without canal dilation ($h_0 = 20$ µm) and with moderate ($h_0 = 40$ µm) and large ($h_0 = 100$ µm) canal dilation. The eye has an initial canal height of 20 µm and an initial elevated IOP of 25 mmHg. The dilation of the Schlemm's canal is limited to a quadrant from the bypass, i.e. $L_d = L/4$.
Figure 12:
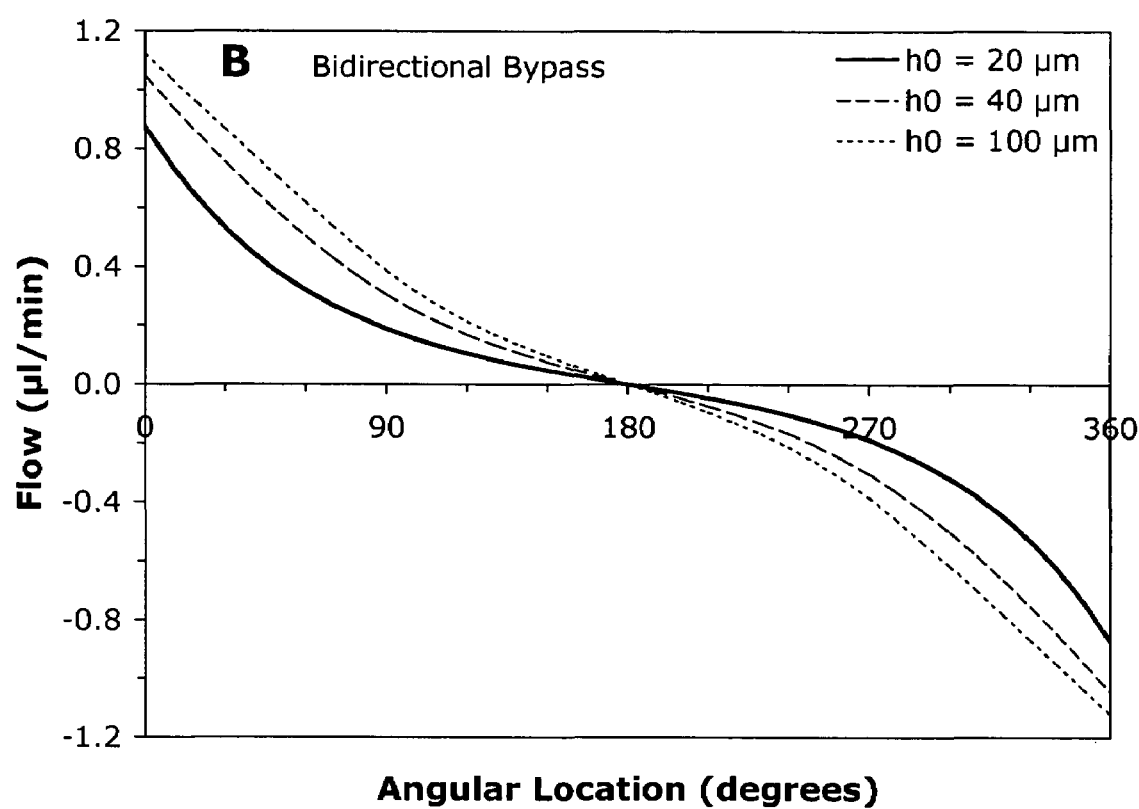
FIG. 12 shows circumferential flow distribution in Schlemm's canal in the presence of (B) a bidirectional trabecular bypass, without canal dilation ($h_0 = 20$ µm) and with moderate ($h_0 = 40$ µm) and large ($h_0 = 100$ µm) canal dilation. The eye has an initial canal height of 20 µm and an initial elevated IOP of 25 mmHg. The dilation of the Schlemm's canal is limited to a quadrant from the bypass, i.e. $L_d = L/4$.

The pressure distribution in Schlemm's canal is shown in FIG. 9 in the presence of a unidirectional trabecular bypass or FIG. 10 in the presence of a bidirectional trabecular bypass, for an average glaucomatous eye with an initial elevated IOP of 25 mmHg. Without the dilation of Schlemm's canal ($h_0$=20 μm), the canal resistance is substantial and the pressure drops rapidly along the circumference from the bypass. With a moderate dilation ($h_0$=40 μm), the canal resistance is significantly lower and the pressure drops slowly along the circumference and more collector channels are exposed to higher pressure. With a large dilation ($h_0$=100 μm), the dilated canal provides little resistance to the circumferential flow and the canal pressure is almost constant along the portion of the dilated canal. In a way, the pressure at the collector channel ostia in the dilated quadrant(s) is effectively the intraocular pressure; therefore, for this segment, it is as if the trabecular meshwork is not present. With the low flow resistance in collector channels, the facility of outflow is expected to increase and the IOP to drop dramatically. The circumferential flow in Schlemm's canal also increases substantially as Schlemm's canal is dilated, as shown in FIGS. 11 and 12. The circumferential flow in Schlemm's canal is effectively zero for the case with no bypass in the outflow model with the collector channels assumed a uniform leaking structure and is negligibly small in the earlier models of Moses (Am J Ophthalmol 1979; 99:585–591), and Johnson and Kamm (Invest Ophthalmol Vis Sci 1981; 24:320–325) for an intact trabecular meshwork and discrete collector channels.

Figure 13:
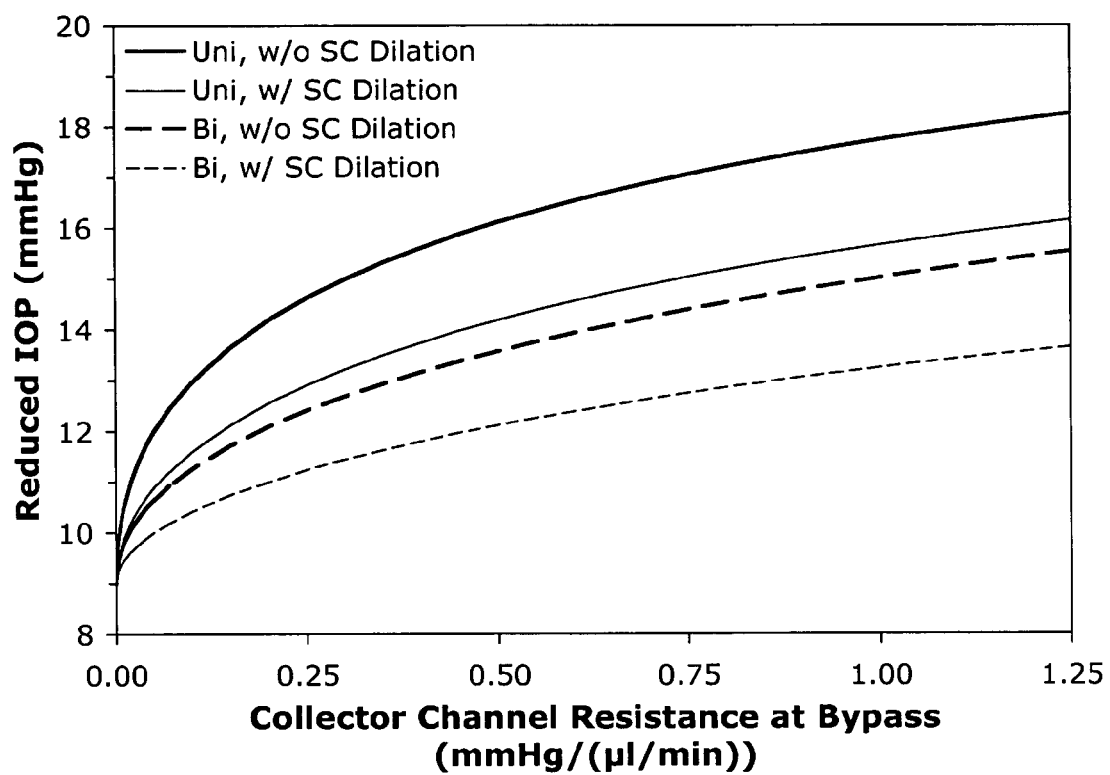
FIG. 13 shows the effect of collector channel dilation in the presence of a unidirectional (Uni) or bidirectional (Bi) bypass on IOP reduction without Schlemm's canal (SC) dilation ($h_0 = 20$ µm) and with moderate canal dilation ($h_0 = 40$ µm). The initial elevated IOP is 25 mmHg. The dilation of the Schlemm's canal and collector channels is limited to a quadrant from the bypass, i.e. $L_d = L/4$.

The dilation of collector channels is also a potentially effective method to further reduce IOP in the presence of a trabecular bypass, as shown in FIG. 13 for an average glaucomatous eye with an elevated IOP of 25 mmHg. FIG. 13 shows the effect of collector channel dilation in the presence of a unidirectional (Uni) or bidirectional (Bi) bypass on IOP reduction without Schlemm's canal (SC) dilation ($h_0$=20 μm) and with moderate canal dilation ($h_0$=40 μm). The initial elevated IOP is 25 mmHg. The dilation of the Schlemm's canal and collector channels is limited to a quadrant from the bypass, i.e. $L_d$=L/4. The IOP drops almost linearly with collector channel resistance from 1.25 to 0.5 mmHg/(μl/min) at the bypass. The rate of reduction in IOP increases when the collector channel resistance falls below 0.5 mmHg/(μl/min). The IOP is reduced to 9 mmHg, the episcleral venous pressure, when the collector channel resistance is completely eliminated at the bypass. In this case, theoretically, an effective bypass is created through the collector channel bed to the aqueous veins and the direct communication between the anterior chamber and the episcleral veins is established.

Figure 14:
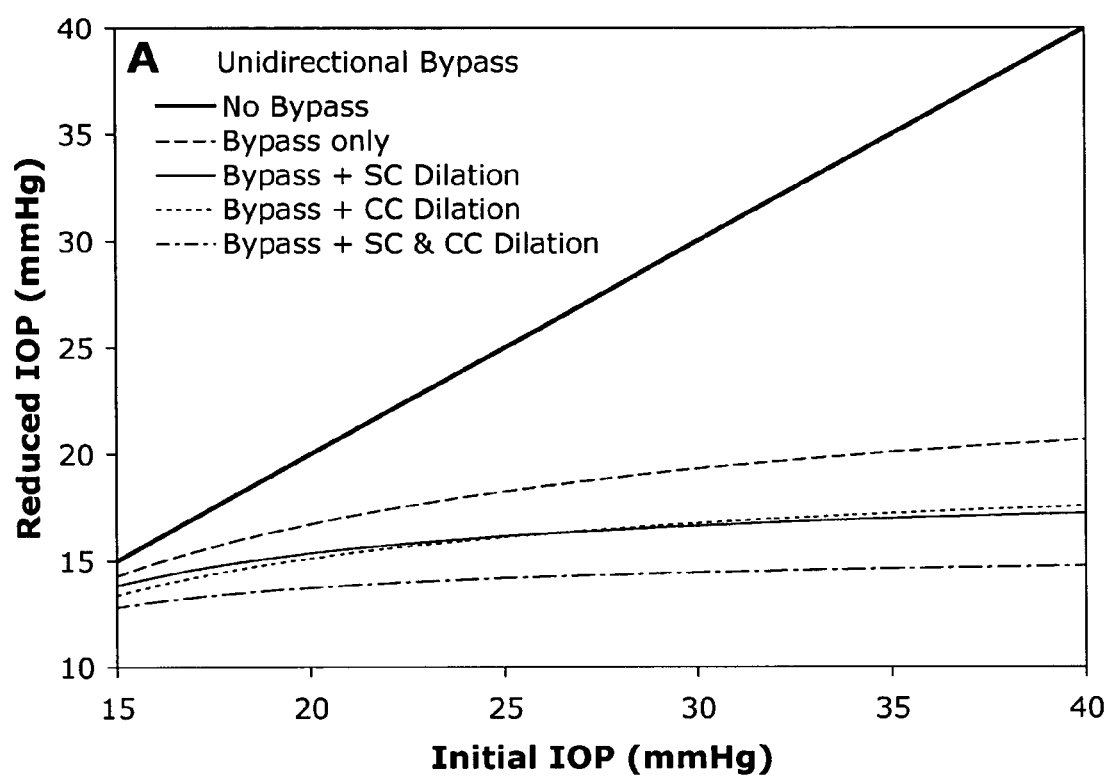
FIG. 14 shows reduced intraocular pressure as a function of initial IOP in the presence of (A) a unidirectional trabecular bypass without and with moderate Schlemm's canal dilation ($h_0 = 40$ µm) and moderate collector channel dilation ($r_{CC0} = 0.5$ mmHg/(µl/min)), for an average eye. The dilation of Schlemm's canal and the collector channels is limited to a quadrant from the bypass, i.e. $L_d = L/4$.
Figure 15:
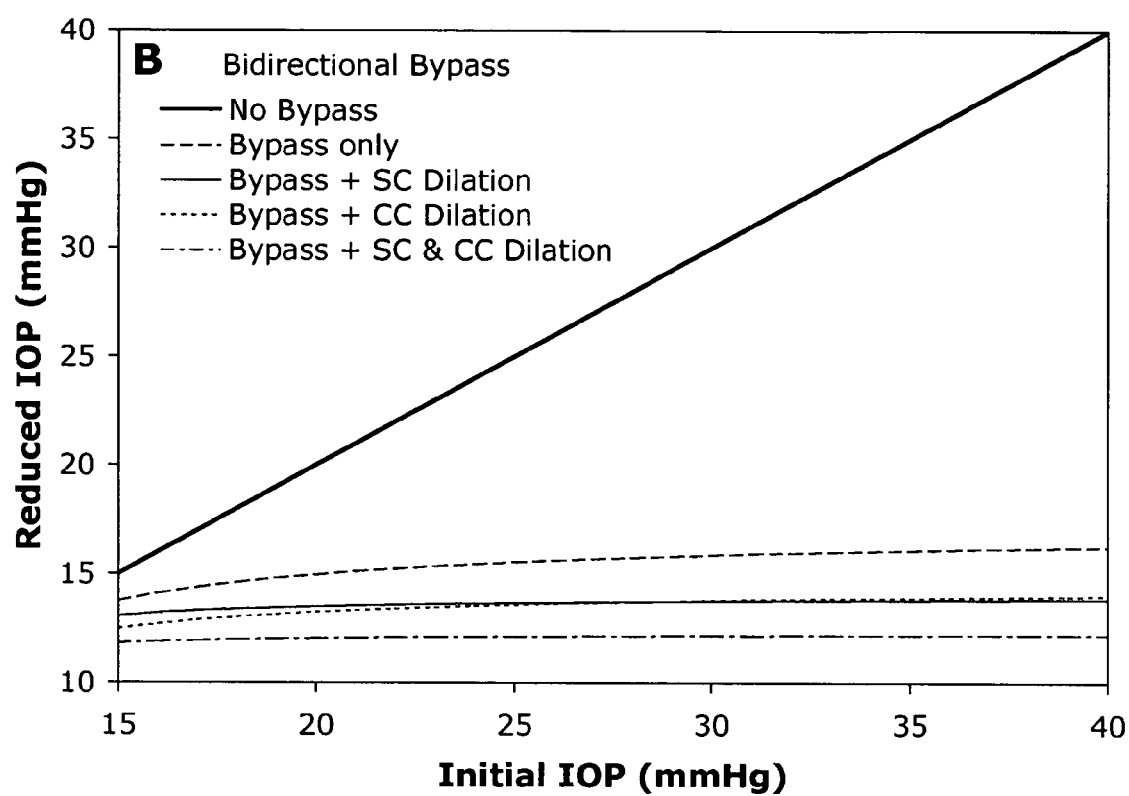
FIG. 15 shows reduced intraocular pressure as a function of initial IOP in the presence of (B) a bidirectional trabecular bypass without and with moderate Schlemm's canal dilation ($h_0$=40 μm) and moderate collector channel dilation ($r_{CC0}$=0.5 mmHg/(μl/min)), for an average eye. The dilation of Schlemm's canal and the collector channels is limited to a quadrant from the bypass, i.e. $L_d$=L/4.

The elevated IOP in glaucomatous eyes can be reduced to normal physiological ranges in the presence of a patent trabecular bypass and the higher the initial IOP, the greater the reduction. With a moderate dilation ($h_0$=40 µm) of Schlemm's canal in conjunction with the bypass, the IOP is further reduced by 2 to 3 mmHg compared to the bypass along (FIGS. 14 and 15). Theoretically, a comparable reduction is also with a moderate dilation ($r_{CC0}$=0.5 mmHg/(µl/min)) of the collector channels with no canal dilation (FIGS. 14 and 15). If both Schlemm's canal and the collector channels are moderately dilated in conjunction with the bypass, the IOP is expected to be further reduced by 3 to 6 mmHg compared to the bypass alone. FIGS. 14 and 15 showed reduced intraocular pressure as a function of initial IOP in the presence of (A) a unidirectional or (B) a bidirectional trabecular bypass without and with moderate Schlemm's canal dilation ($h_0$=40 µm) and moderate collector channel dilation ($r_{CC0}$=0.5 mmHg/(µl/min)), for an average eye. The dilation of Schlemm's canal and the collector channels is limited to a quadrant from the bypass, i.e. $L_d$=L/4.

Figure 16:
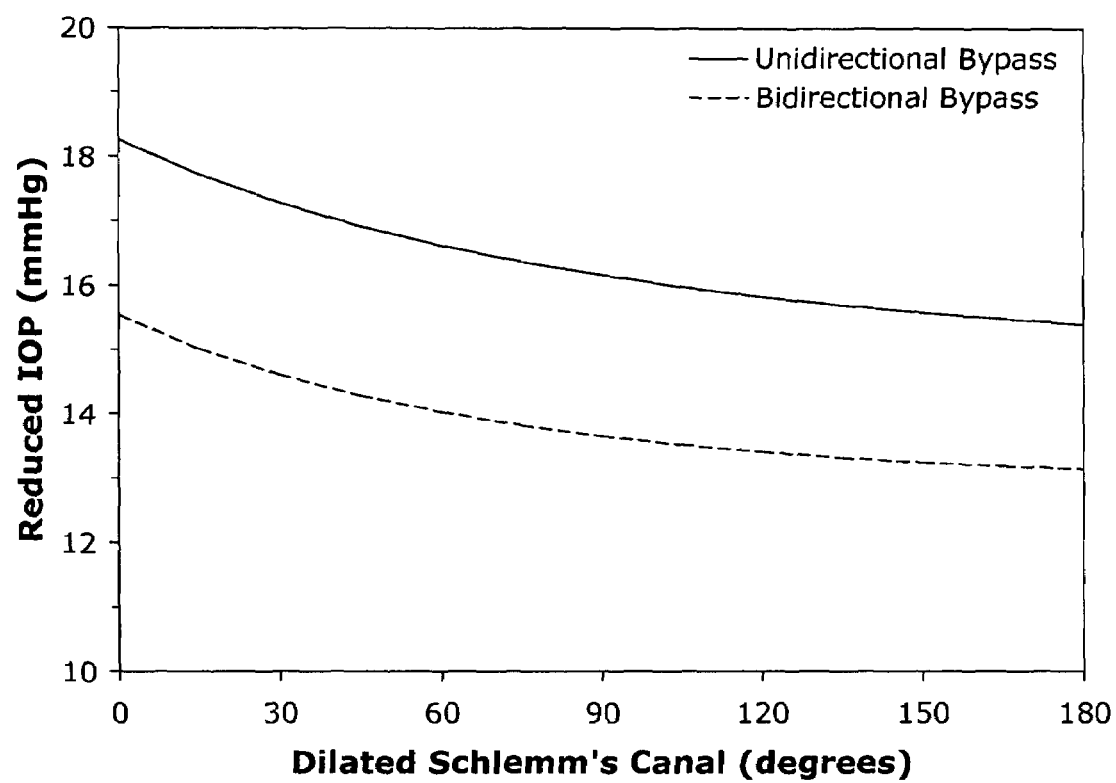
FIG. 16 shows reduced intraocular pressure as a function of dilated length of Schlemm's canal in the presence of a unidirectional or a bidirectional trabecular bypass with moderate Schlemm's canal dilation ($h_0$=40 μm). The initial elevated IOP is 25 mmHg.

The dependency of the IOP reduction on the dilated length ($L_d$) of Schlemm's canal is exhibited in FIG. 16, for an average eye with an elevated IOP of 25 mmHg. The IOP drops relatively fast when the dilation length is immediate one quadrant (L/4, 90°) beyond the bypass. Increasing the dilation length beyond L/4 (90°) provides diminishing further reduction in. In the case of a unidirectional bypass, the IOP drops from 25 to 18.3 mmHg without canal dilation (bypass only), to 16.2 mmHg with the first quadrant of the canal moderately expanded, and to 15.4 mmHg with the next quadrant of the canal also expanded. In the case of a bidirectional bypass, the IOP drops from 25 to 15.5 mmHg without canal dilation (bypass only), to 13.7 mmHg with the first quadrant of the canal moderately expanded, and only to 13.1 mmHg with the next quadrant of the canal also expanded.

FIG. 16 showed reduced intraocular pressure as a function of dilated length of Schlemm's canal in the presence of a unidirectional or a bidirectional trabecular bypass with moderate Schlemm's canal dilation ($h_0$=40 µm). The initial elevated IOP is 25 mmHg.

Flow Model Discussion

Normally, the aqueous flow in Schlemm's canal is relatively small when the trabecular meshwork is intact. Moses (1979) studied the circumferential flow in Schlemm's canal between two collector channels and examined the effect of canal dimension on IOP, while modeling the cross section of Schlemm's canal as an ellipse. Johnson and Kamm (1983) extended this model and introduced a flexible inner wall to a rectangle shaped Schlemm's canal to study the effect of canal collapse. In both studies, the localized circumferential flow is small at 0.04 µl/min (i.e. total outflow of 2.4 µl/min distributed over 30 equally spaced collector channels over 2 directions) and the aqueous travels a short distance (about 0.6 mm on average) to reach a collector channel. With a normal canal resistance, about 1 mmHg/(µl/min)/mm, Schlemm's canal does not provide any significant resistance to this small physiological circumferential flow, unless the canal is dramatically collapsed. Therefore, the conclusion of these previous investigations is that Schlemm's canal offers little resistance to outflow except in extremely collapsed condition.

In the present study, the constructing of a trabecular bypass creates significant larger circumferential flow when a compared to the intact trabecular meshwork case studied by previous investigators. Once a patent trabecular bypass is present, the majority of outflow enters Schlemm's canal through the bypass. The circumferential flow in the vicinity of the bypass increases to ~1 µl/min and this amount of aqueous is drained to collector channels over a limited stretch of canal bed (FIGS. 11 and 12). The normal-sized canal provides a notable resistance to such a relatively large flow, compared to previously studied flow rates that are 25 times less. On average, a patent trabecular bypass is expected to lower the elevated IOP in primary open angle glaucoma to normal physiological levels. Statistically, some eyes would perform better than the average while other eyes, especially ones with smaller Schlemm's canals, may see less reduction in IOP. The current study shows that a patent moderate dilation ($h_0$=40 µm) of the Schlemm's canal in conjunction with a trabecular bypass could provide, on average, an additional 2 to 3 mmHg reduction in IOP; this reduction is expected to be even greater for eyes with smaller canals.

In the presence of a trabecular bypass, the Schlemm's canal pressure is highest at the bypass, equal to IOP, and decreases rapidly along the circumference due to the significant canal resistance to circumferential flow. When Schlemm's canal is dilated in conjunction with a trabecular bypass, the canal resistance is reduced and the pressure gradient along the dilated circumference is lessened, as shown in FIGS. 9 and 10. If the canal is dilated to such extent that there is not much pressure gradient in the dilated segment of the canal, the pressure in that part of canal is essentially the IOP; therefore, it seems that the trabecular meshwork along the dilated part of canal does not even exist. In a way, Schlemm's canal dilation in conjunction with a trabecular bypass is analogous to a partial trabeculotomy, but only requires a small bypass hole through the trabecular meshwork rather than a large-scale removal of trabecular meshwork.

Figure 17:
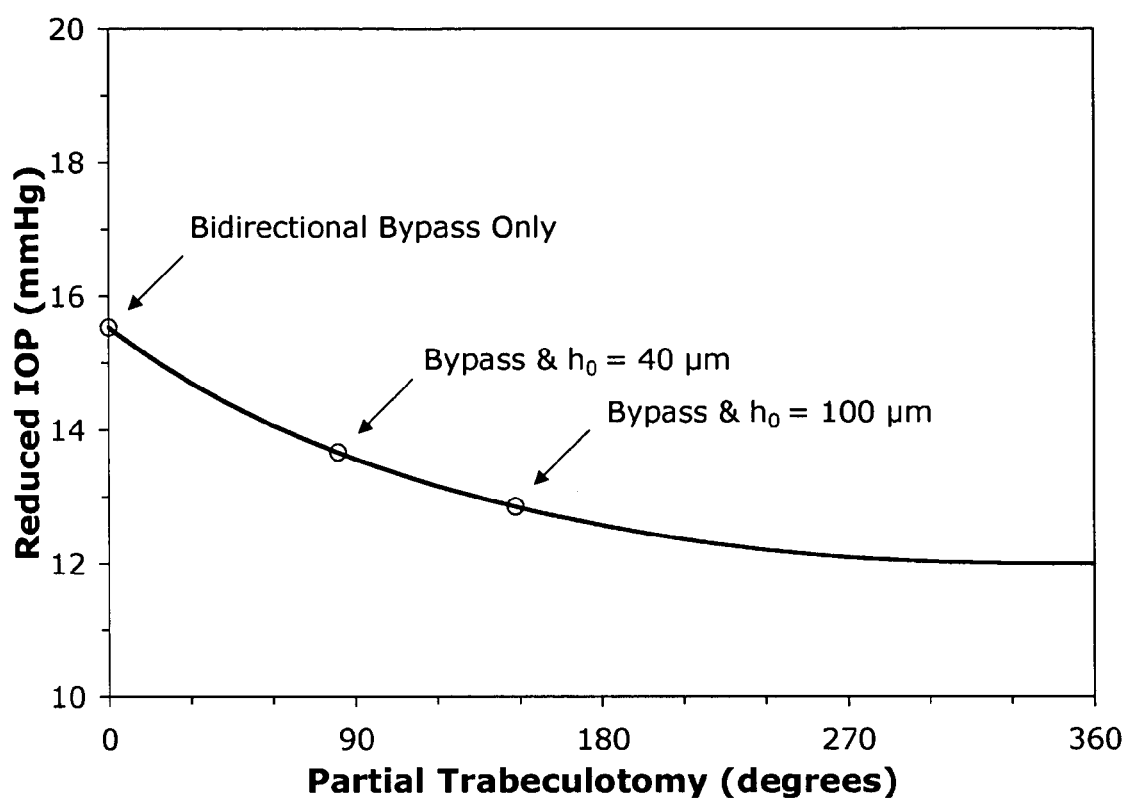
FIG. 17 shows effect of partial trabeculotomy on IOP reduction. The bidirectional bypass is regarded as a zero degree partial trabeculotomy. The initial elevated IOP is 25 mmHg.

In partial trabeculotomy, a section of Schlemm's canal outer wall is exposed to the anterior chamber. The collector channels behind the removed segment of trabecular meshwork are directly connected to the anterior chamber and the pressure at the ostia of these collector channels is the intraocular pressure. A portion of aqueous humor can straightforwardly enter the less resistant collector channels. Through the canal opening, another portion of aqueous humor travels circumferentially in Schlemm's canal to reach the collector channels behind the remaining trabecular meshwork. Probably, a very small amount of aqueous humor still passes through the remaining meshwork. The current model can be easily modified to calculate the IOP reduction in the case of a partial trabeculotomy. FIG. 17 illustrates the reduced IOP as the function of removed circumference of trabecular meshwork, for a typical glaucomatous eye with an elevated IOP of 25 mmHg. The IOP shows the biggest drop to 15.5 mmHg at the mere presence of a trabecular bypass. The IOP is further reduced as the meshwork is progressively removed, but the rate of reduction is fastest at the beginning and slows down as more meshwork is removed. The IOP is reduced to 12 mmHg when the meshwork is completely removed. Comparing FIG. 17 with FIG. 8, a moderate dilation ($h_0$=40 µm) of the canal in conjunction with a bidirectional trabecular bypass demonstrates a similar effect on IOP reduction to a continuous 90° (three clock hours) trabeculotomy, while a large dilation ($h_0$=100 µm) is similar to a 150° (five clock hour) trabeculotomy. It is worth noting that a moderate dilation of Schlemm's canal will likely induce a smaller tissue healing process than an equivalent partial trabeculotomy.

FIG. 17 showed the effect of partial trabeculotomy on IOP reduction. The bidirectional bypass is regarded as a zero degree partial trabeculotomy. The initial elevated IOP is 25 mmHg.

During viscocanalostomy procedures, the aqueous humor was observed to percolate through the exposed trabeculo-Descemet's membrane. It was postulated that this window of Descemet membrane was the egress route for aqueous to bypass the highly resistant trabecular meshwork. Spiegel et al. (Arch Clin Exp Ophthalmol 2002; 240:111–113) found that the outflow facility through the center of Descemet's membrane in rabbit eyes was too low to be effective in the relief of elevated IOP. Spiegel et al., however, did not report whether the permeability at the periphery of Descemet's membrane is comparable. Johnson and Johnson (J. Glaucoma 2001; 10:55–67), through the histological studies, postulated that damage to inner wall of Schlemm's canal and the juxtacanilicular tissue, during the unroofing procedure and during the canal dilation with injection of viscoelastic material, probably reduced the outflow resistance in the region. Smit and Johnstone (Ophthalmology 2002; 109: 786–792), through cannulation and viscoelastic dilation of primate and human autopsy eyes, observed that the canal walls were disrupted in both the region of cannulation and the region of viscoelastic dilation as well as the marked dilation of Schlemm's canal and associated collector channels.

Clearly, for viscocanalostomy to work as a successful glaucoma surgery procedure to reduce IOP, a low resistance region has to be created proximal to Schlemm's canal so that a large portion of the aqueous outflow can bypass the highly resistant trabecular meshwork to enter the scleral lake and Schlemm's canal. Laser goniopuncture of trabeculo-Descemet's membrane was performed postoperatively in many viscocanalostomy studies and was shown effective for the cases in which there was insufficient percolation of aqueous humor through the membrane and the IOP was not lowered to the target level. The goniopuncture procedure created a direct communication between the anterior chamber and the scleral lake and Schlemm's canal, effecting a trabecular bypass. The present study demonstrates the theoretical benefit of an enlarged Schlemm's canal in conjunction with a non-resistant passageway through the trabecular meshwork (trabecular bypass) on reducing IOP. How the tissue will respond to a moderate dilation of Schlemm's canal is unknown. However, long term IOP reduction has been reported in many patients who underwent viscocanalostomy procedure. The increased circumferential flow in the canal, the associated higher shear stresses on endothelial cells of the canal wall, and the lower trans-trabecular pressure present a fresh environment for tissue remodeling processes. To maintain a long-term patency of the dilated canal maybe vital to the success of transferring the concept into reality. The advance in imaging technology to be ultimately able to monitor the canal dimension in vivo could become critical in assessing the mechanism of current and future surgical treatments on glaucoma.

Smit and Johnstone also observed the marked dilation of collector channel ostia and associated collector channels in the sclera in their visoelastic dilation experiments on primate and human Schlemm's canals. The present study demonstrates that the dilation of collector channels in conjunction of a trabecular bypass can provide notable benefit in the reduction of IOP in glaucomatous eyes, as it creates an extremely low resistance route for aqueous humor to flow from the anterior chamber to the aqueous veins. While it is generally regarded that, in viscocanalostomy, the aqueous humor enters Schlemm's canal and the scleral lake via either the trabeculo-Descemet's window, or the disrupted region of canal inner wall and underlying juxtacanilicular tissue, or perhaps both, bypassing the remaining highly resistant trabecular meshwork, the escape route of the aqueous humor from there is not clearly understood. Certainly, if the dilated canal and collector channels remain patent and the cut ends of the canal do not heal to the extent that they restrict or block the circumferential flow in the long term, the aqueous humor can be drained via the conventional outflow pathway.

Other outflow pathways originating from the scleral lake, created after the removal of the deep scleral flap in a viscocanalostomy procedure, have been postulated, including uveoscleral drainage, subconjunctival filtration, formation of aqueous veins; although, it was also found that the size of the lake had no correlation to the reduction in IOP. The scleral lake would behave like a large collector channel in a mathematic sense if a substantial amount of aqueous humor could be drained from the lake with little resistance. In the case of dilation of Schlemm's canal (and collector channels) in conjunction with a trabecular bypass, the aqueous humor still relies on the physiologic outflow pathway as the main passageway so that, even with large canal dilation and reduction in collector channel resistance, the episcleral venous pressure in downstream maintains the lower pressure limit to prevent hypotony.

Multi-Stent Therapy

Multi-stent therapy refers to the intentional placement of a stent in each of several locations in Schlemm's canal. Since Schlemm's canal has measurable resistance to flow at physiological flow rates, the stents are placed close to concentrations of collector ducts or a large collector and distributed around Schlemm's canal to maximize the impact of multiple stents. Numerical modeling of the outflow system of the eye utilizing the spatial variation in the outflow resistance produced by the collector channels is used to predict the preferred locations of the multiple stents to achieve the best improvement in outflow facility.

Some aspects of the invention relate to a method for implanting a trabecular stent to lower intraocular pressure of an eye, comprising: (a) providing the trabecular stent, wherein the stent comprises an inlet terminal and an outlet terminal; (b) means for identifying a target collector channel region that is connects to peripheral of Schlemm's canal; and (c) placing the trabecular stent through trabecular meshwork, wherein the inlet terminal is exposed to an anterior chamber and the outlet terminal is exposed to about the target collector channel region. Further, the step of placing the trabecular stent through the trabecular meshwork is by an ab interno procedure or by an ab externo procedure. In one embodiment, the target collector channel region comprises a large collector channel with an ostium, wherein the outlet terminal is placed at about the ostium of the large collector channel.

In one preferred embodiment, the trabecular stent is an axisymmetric stent or loaded with anti-glaucoma agent. In another embodiment, the means for identifying the target collector channel region is by observing the reflux of blood toward Schlemm's canal. In still another embodiment, the means for identifying the target collector channel region is by trabecular flow modeling, by optical coherence tomography, by light or by ultra-high frequency ultrasound biomicroscopy. The step of placing the trabecular stent through the trabecular meshwork is by an ab interno procedure or an ab externo procedure.

Some aspects of the invention relate to a method further comprising a step of implanting a second trabecular stent at a second target collector channel region, wherein the second target collector channel region is adjacent to the first target collector channel region or not adjacent to the first target collector channel region, preferably at about 180 degree from the first target collector channel region.

Some aspects of the invention relate to a method for achieving a target intraocular pressure of an eye, comprising: (a) providing a bypass flow model, wherein the model simulates hydrodynamic aqueous flow from an anterior chamber to aqueous cavity, and wherein the model comprises a data input requirement and a data output statement; (b) identifying aqueous cavity parameters; (c) selecting a trabecular stent, wherein the stent comprises an inlet terminal and at least one outlet terminal; (c) performing the bypass flow model by keying in the data input requirement, including at least one parameter selected from the aqueous cavity parameters; and (d) obtaining the data output statement through the model, wherein the statement includes a decision selected from a group consisting of a number of trabecular stents needed, a location of the trabecular stent implanted, and type of the trabecular stent. The "aqueous cavity" is herein intended to mean Schlemm's canal and any aqueous conducting channel downstream of Schlemm's canal.

In one embodiment, the aqueous cavity parameters comprise collector channel resistance, Schlemm's canal resistance, length of Schlemm's canal, height of Schlemm's canal, and width of Schlemm's canal. In another embodiment, the data input requirement is selected from a group consisting of a patient's intraocular pressure, episcleral venous pressure, conventional outflow, trabecular meshwork resistance, facility of outflow, viscosity of aqueous humor. FIG. 6 shows the aqueous cavity parameters and the data input requirement for the bypass flow model, including average parameters for a normal eye with healthy trabecular meshwork.

Micro-Anatomy: In-vitro

Several investigators have conducted research in the area of the micro-anatomy of Schlemm's canal, the collector channels, and the circulatory system of the eye. Some of the most detailed work was performed from 1934 to 1955. Of particular note is the work of G. Dvorak-Theobald (Trans Amer Ophthal Soc 1934; 32:574–595) and N. Ashton (Brit J Ophthal 1953; 37:577–586). Dvorak-Theobald studied 3 eyes using serial sections that were carefully observed to determine the location and extent of collector channels extending from Schlemm's canal.

Figure 18:
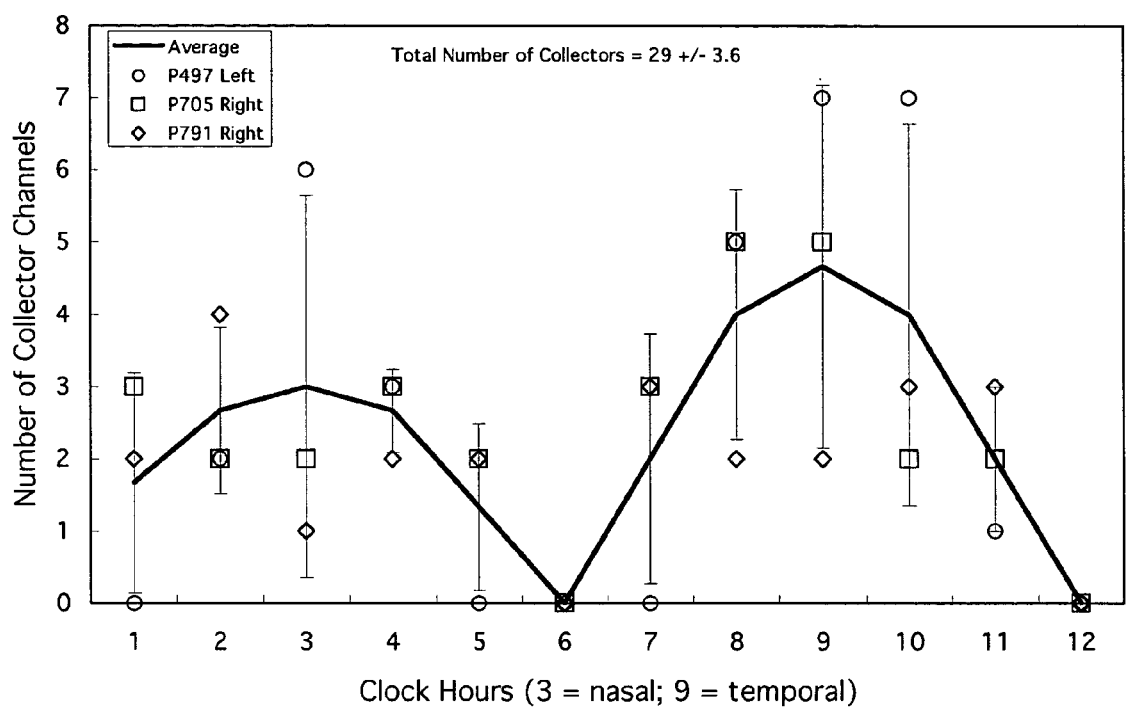
FIG. 18 shows plot of collector channel distribution from three eye samples.

Using image-processing techniques, we extracted the angular location of each of the collector ducts, drawn as line segments extending from the outer edge of Schlemm's canal, from Dvorak-Theobald's figures. Subsequently, we grouped the collector channel locations according to a standardized clock hour system where 3 o'clock is nasal and 9 o'clock is temporal. The resulting spatial distribution of the collector channels in these three eyes is depicted in FIG. 18 (derived from Trans Amer Ophthal Soc 1934; 32:574–595 and Amer J of Ophthal 1955; 39:65–89). It is clear from this figure, that the collector channels are concentrated in the nasal and temporal regions of the eye with the greatest concentration in the temporal region. Since the data are rather limited, the standard deviations (shown as error bars in the plot) are rather large; however, the average curve drawn on the plot serves as a first order approximation of the spatial distribution of the collector channels for the average eye. In one embodiment, the average distribution of the collectors is used as an input boundary condition for the numerical model of the outflow system of the eye.

Since the serial sections are each 15 μm thick, it is possible to estimate the size of the various collector channels by noting how many sections each collector channel was noted. Note, that despite significant eye-to-eye variations in the number and size of the collector channels, the largest channels are consistently located between 3:20 and 3:55 on the nasal side and between 8:45 and 9:30 on the temporal side. This first order consistency of the location of the largest collector channels provides useful guidance for optimal stent placement. As data continue to be collected on these, the mapping should become more refined and provide additional information and confidence on the preferred locations. In some aspects of the invention, the bypass flow model can use the "average-eye" outflow derived from the three eyes as depicted in FIG. 18 (derived from Trans Amer Ophthal Soc 1934; 32:574–595 and Amer J of Ophthal 1955; 39:65–89), a "specific-eye" flow obtained from an individual, or the "universal-eye" flow derived from future morphological data.

Micro-Anatomy: In-vivo

The in-vitro information described above is useful means to achieve a first-order estimate of the general distribution of collector channels that is viable for input to the numerical model and to provide first order information on stent placement for the average eye. A step beyond this is to determine the collector channel distribution for a given eye using an in-vivo method so that stent placement can be tailored to the individual. Significant work is going on in the area of anterior segment diagnostics such as Optical Coherence Tomography (OCT) and Ultra-High Frequency Ultrasound Biomicroscopy (UHF-UBM) where imaging resolution is approaching that necessary to map collector channel locations in the live eye. After complete mapping using these instruments or an upcoming instrument, the map can be input to the ocular outflow model and be used to determine the preferred locations of the stent or stents to achieve the best improvement of outflow facility.

As illustrated in examples and the foregoing description, a flow bypass model is provided, once the target IOP is specified, capable of determining output conditions to assist a physician's therapeutic decision, such as how many implants, what type of implant (uni- or bidirectional flow), where the implant goes, a second stent implantation and the like.

From the foregoing description, it should be appreciated that a novel method and simulation system enabling targeted placement of stent(s) for surgical treatment of glaucoma have been disclosed for reducing intraocular pressure. While the invention has been described with reference to specific embodiments, the description is illustrative of the invention and is not to be construed as limiting the invention. Various modifications and applications of the invention may occur to those who are skilled in the art, without departing from the true spirit or scope of the invention. The breadth and scope of the invention should be defined only in accordance with the principles of the present invention.

What is claimed is:

1. A method of treating a patient with elevated intraocular pressure using a treatment recommendation which provides at least one of a recommended location of a stent implantation and a recommended number of stents to be implanted, the method comprising:

acquiring a treatment recommendation comprising said at least one of said recommended location of said stent implantation and said recommended number of stents to be implanted for the patient, the treatment recommendation based on a baseline intraocular pressure of the patient, at least one of a target intraocular pressure and a target reduction in intraocular pressure for the patient, and at least one aqueous cavity datum, wherein the at least one aqueous cavity datum is selected from the group of a collector channel resistance, a Schlemm's canal resistance, a length of a segment of Schlemm's canal, a height of Schlemm's canal, and a width of Schlemm's canal; and treating the patient according to the treatment recommendation.

2. The method of claim 1, wherein the recommended location of a stent implantation comprises a distance from a collector channel.

3. The method of claim 2, wherein the distance is measured along Schlemm's canal.

4. The method of claim 1,
wherein the treatment recommendation is also based on at least one additional ocular datum, the at least one additional ocular datum selected from the group of an episcleral venous pressure, a trabecular meshwork resistance, a facility of outflow, and a viscosity of aqueous humor.

5. The method of claim 1, wherein the treating comprises implanting one or more stents to reduce the elevated intraocular pressure.

6. A method of treating a patient with elevated intraocular pressure using a treatment recommendation, the method comprising:

acquiring a treatment recommendation comprising at least one of a recommended location of a stent implantation and a recommended number of stents to be implanted for the patient, the treatment recommendation based on a baseline intraocular pressure of the patient, at least one of a target intraocular pressure and a target reduction in intraocular pressure for the patient, and at least one of a location of at least one collector channel and a distribution of a plurality of collector channels; and treating the patient according to the treatment recommendation.

7. The method of claim 6, wherein the recommended location of a stent implantation is selected from the group consisting of nasal, temporal, a quadrantic position, and a clock-hour position.

8. The method of claim 6, wherein the distribution of a plurality of collector channels is determined by imaging the patient.

9. The method of claim 6, wherein the distribution of a plurality of collector channels is determined at least in part from statistical data from eyes other than the patient's eyes.

10. The method of claim 6, wherein the treating comprises implanting one or more stents to reduce the elevated intraocular pressure.

* * * * *

UNITED STATES PATENT AND TRADEMARK OFFICE
CERTIFICATE OF CORRECTION

PATENT NO. : 7,192,412 B1
APPLICATION NO. : 10/662696
DATED : March 20, 2007
INVENTOR(S) : Jianbo Zhou et al.

It is certified that error appears in the above-identified patent and that said Letters Patent is hereby corrected as shown below:

Title page, column 2, line 3 after "II," delete ":".

Title page, column 2, lines 13-14, delete "Ophthalmology;" and insert -- Ophthalmology & Visual Science; --.

Column 2, line 64, delete "trail" and insert -- trial --.

Column 4, line 26, delete "effect tis" and insert -- effect is --.

Column 6, line 7, after "glaucoma" insert -- . --.

Column 6, line 16, delete "height" and insert -- heights --.

Column 7, line 37, after "non-" delete "diluted" and insert -- dilated --.

Column 7, line 37, delete "diluted" and insert -- dilated --.

Column 7, line 41, after "flow" delete "is" and insert -- in --.

Column 10, line 41, before "patient" delete "his" and insert -- this --.

Column 12, line 20, delete "239" and insert -- 230 --.

Column 14, line 28, delete "visoelastic." And insert -- viscoelastic. --.

Column 17, line 16, before "-$L_d$" insert -- L --.

Column 17, line 42, delete, after "it" delete "has" and insert -- had --.

Column 17, line 65, delete "resistance" and insert -- resistances --.

Column 18, line 47, delete "99" and insert -- 88 --.

Column 19, line 10, delete "along" and insert -- alone --.

Column 20, line 3, before "compared" delete "a".

UNITED STATES PATENT AND TRADEMARK OFFICE
CERTIFICATE OF CORRECTION

PATENT NO.        : 7,192,412 B1
APPLICATION NO. : 10/662696
DATED             : March 20, 2007
INVENTOR(S)       : Jianbo Zhou et al.

It is certified that error appears in the above-identified patent and that said Letters Patent is hereby corrected as shown below:

Column 21, line 63, delete "visoelastic" and insert -- viscoelastic --.

Signed and Sealed this

Eleventh Day of September, 2007

JON W. DUDAS
*Director of the United States Patent and Trademark Office*